US006060305A

United States Patent [19]

Royer et al.

[11] Patent Number: 6,060,305

[45] Date of Patent: *May 9, 2000

[54] NON-TOXIC, NON-TOXIGENIC, NON-PATHOGENIC FUSARIUM EXPRESSION SYSTEM

[75] Inventors: John C. Royer; Donna L. Moyer, both of Davis; Yoder T. Wendy, Winters; Jeffrey R. Shuster, Davis, all of Calif.

[73] Assignee: Novo Nordisk Biotech, Inc., Davis, Calif.

[ * ] Notice: This patent issued on a continued prosecution application filed under 37 CFR 1.53(d), and is subject to the twenty year patent term provisions of 35 U.S.C. 154(a)(2).

[21] Appl. No.: 08/816,915

[22] Filed: Mar. 13, 1997

Related U.S. Application Data

[63] Continuation-in-part of application No. 08/726,105, Oct. 4, 1996, abandoned, which is a continuation-in-part of application No. 08/404,678, Mar. 15, 1995, abandoned, which is a continuation-in-part of application No. 08/269,449, Jun. 30, 1994, abandoned.

[51] Int. Cl.[7] .......... C12N 1/14

[52] U.S. Cl. .......... 435/254.7

[58] Field of Search .......... 435/69.1, 172.3, 435/254.7, 484

[56] References Cited

U.S. PATENT DOCUMENTS

| | | | |
|---|---|---|---|
| 4,041,189 | 8/1977 | Towersey et al. | 426/656 |
| 5,446,138 | 8/1995 | Blaiseu et al. | 536/23.74 |

OTHER PUBLICATIONS

Dickman et al., Mol. Gen. Genet. 235:458–462 (1992).
Daboussi et al., Curr. Genet. 15:453–456 (1989).
Thrane, Journal of Microbiological Methods 12:23–39 (1990).
Nelson et al. [Clinical Microbiology Reviews 7(4):479–504 (1994).

*Primary Examiner*—Remy Yucel
*Attorney, Agent, or Firm*—Steve Zelson, Esq.; Robert L. Starnes; Cheryl Agris, Esq.

[57] ABSTRACT

The present invention relates non-toxic, non-toxigenic, non-pathogenic recombinant Fusarium host cells of the section Discolor or a teleomorph or synonym thereof, comprising a nucleic acid sequence encoding a heterologous protein operably linked to a promoter.

1 Claim, 16 Drawing Sheets

NON-TOXIC, NON-TOXIGENIC, NON-PATHOGENIC FUSARIUM EXPRESSION SYSTEM

This application is a continuation-in-part of Ser. No. 08/726,105, filed Oct. 4, 1996, now abandoned, which is a continuation-in-part of of Ser. No. 08/404,678 filed Mar. 15, 1995, now abandoned, which is a continuation-in-part of Ser. No. 08/269,449 filed Jun. 30, 1994, now abandoned, which are incorporated herein by reference.

BACKGROUND OF THE INVENTION

1. Field of the Invention

The present invention relates to host cells useful in the production of recombinant proteins. In particular, the invention relates to non-toxic, non-toxigenic, and non-pathogenic fungal host cells of Fusarium which can be used in the high-level expression of recombinant proteins, especially enzymes. The invention further relates to promoter and terminator sequences which may be used in such a system.

2. Description of the Related Art

The use of recombinant host cells in the expression of heterologous proteins has in recent years greatly simplified the production of large quantities of commercially valuable proteins, which otherwise are obtainable only by purification from their native sources. Currently, there is a varied selection of expression systems from which to choose for the production of any given protein, including prokaryotic and eukaryotic hosts. The selection of an appropriate expression system will often depend not only on the ability of the host cell to produce adequate yields of the protein in an active state, but also to a large extent may be governed by the intended end use of the protein.

Although mammalian and yeast cells have been the most commonly used eukaryotic hosts, filamentous fungi have now begun to be recognized as very useful as host cells for recombinant protein production. Examples of filamentous fungi which are currently used or proposed for use in such processes are *Neurospora crassa, Acremonium chrysogenum, Tolypocladium geodes, Mucor circinelloides* and *Trichoderma reesei, Aspergillus nidulans, Aspergillus niger* and *Aspergillus oryzae.*

Certain species of the genus Fusarium have been used as model systems for the studies of plant pathogenicity and gene regulation such as *Fusarium oxysporum* (Diolez et al., 1993, Gene 131:61–67; Langin et al., 1990, Curr. Genet. 17:313–319; Malardier et al., 1989, Gene 78:147–156 and Kistler and Benny, 1988, Curr. Genet. 13:145–149), *Fusarium solani* (Crowhurst et al., 1992, Curr. Genet. 21:463–469), and *Fusarium culorum* (Curragh et al., 1992, Mycol. Res. 97:313–317). These Fusarium sp. would not be suitable commercially for the production of heterologous proteins because of their undesirable characteristics such as being plant pathogens or because they produce unsafe levels of mycotoxin. Dickman and Leslie (1992, Mol. Gen. Genet. 235:458–462) discloses the transformation of *Gibberella zeae* with a plasmid containing nit-2 of *Neurospora crassa*. The strain of *Gibberella zeae* disclosed in Dickman and Leslie is a plant pathogen and produces zearalenone, an estrogenic mycotoxin. Sanchez-Fernandez et al. (1991, Mol. Gen. Genet. 225:231–233) discloses the transformation of *Gibberella fujikoroi* carrying a niaD mutation with a plasmid containing the *Aspergillus niger* niaD gene.

An ideal expression system is one which is substantially free of protease and mycotoxin production, also substantially free of large amounts of other endogenously made secreted proteins, and which is capable of higher levels of expression than known host cells. The present invention now provides new Fusarium expression systems which fulfill these requirements.

SUMMARY OF THE INVENTION

The present invention relates to non-toxic, non-toxigenic, non-pathogenic recombinant Fusarium host cell in the section Discolor (also known as the section Fusarium) or a synonym or teleomorph thereof, comprising a nucleic acid sequence encoding a heterologous protein operably linked to a promoter. The host cells and methods of the present invention are unexpectedly more efficient in the recombinant production of certain fungal enzymes than are other known fungal species, such as *Aspergillus niger Aspergillus oryzae*, or *Fusarium oxysporum.*

The invention also relates to methods for production of heterologous proteins, comprising culturing a host cell of the present invention under conditions conducive to expression of the protein, and recovering the protein from the culture. In a preferred embodiment, the protein is a fungal protein, most preferably a fungal enzyme. Using the method of the present invention, at least about 0.5 g heterologous protein/l host cell is produced.

The invention further relates to a promoter sequence derived from a gene encoding a *Fusarium oxysporum* trypsin-like protease or a fragment thereof having substantially the same promoter activity as said sequence. The sequence of the promoter is shown in SEQ ID NO:5.

Additionally, the invention relates to a terminator sequence derived from a gene encoding a *Fusarium oxysporum* trypsin-like protease or a fragment thereof having substantially the same terminator activity as said sequence. The sequence of the terminator is shown in SEQ ID NO:6.

BRIEF DESCRIPTION OF THE FIGURES

FIG. 8A shows the results of an assay for CAREZYME®. FIG. 8B shows SDS-PAGE analysis of the production of CAREZYME® in said *Fusarium graminearum*. Lane 1: molecular size markers; lane 2:20 hrs.; lane 3:50 hrs.; lane 4:70 hrs.; lane 5:90 hrs.; land 6:120 hrs.; lane 7:140 hrs.; lane 8:160 hrs.

Figure 9A:
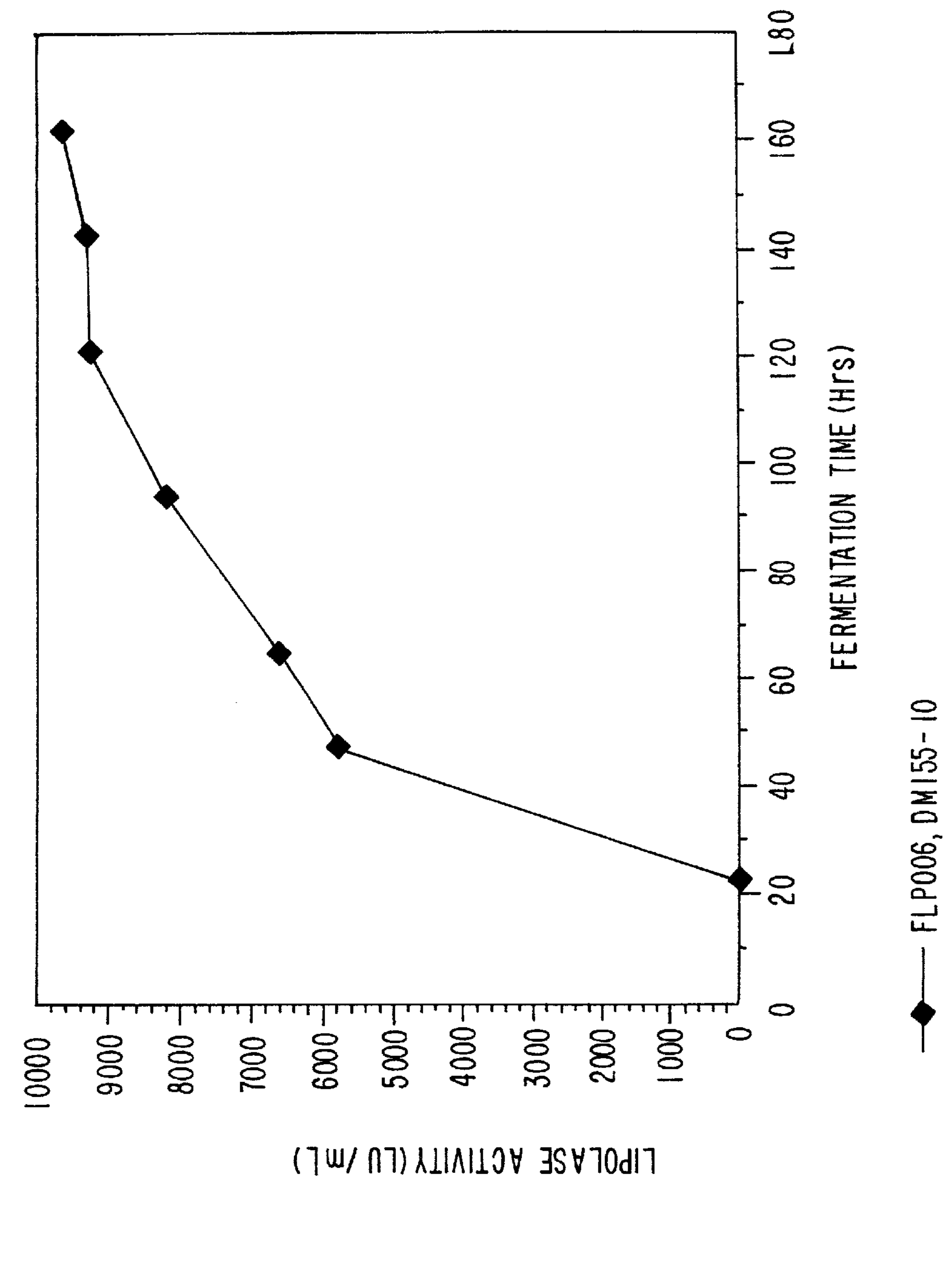
Figure 9B:
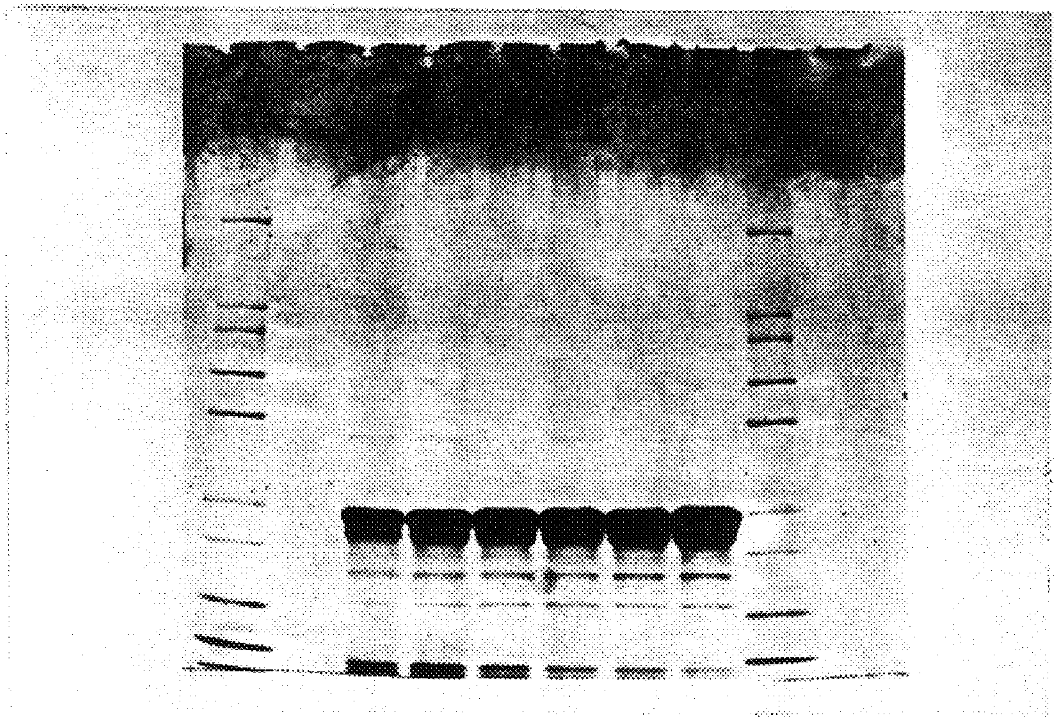

FIGS. 9A and 9B show the level of expression of LIPOLASE® when DSM 155-10 is fermented in *Fusarium graminearum* from 20–160 hrs. FIG. 9A shows the results of an assay for LIPOLASE®. FIG. 9B shows SDS-PAGE analysis of the production of LIPOLASE® in said *Fusarium graminearum*. Lane 1: molecular size markers; lane 2: 20 hrs.; lane 3: 50 hrs.; lane 4: 60 hrs.; lane 5: 90 hrs.; lane 6: 120 hrs.; lane 7: 140 hrs.; lane 8: 160 hrs.

Figure 10:
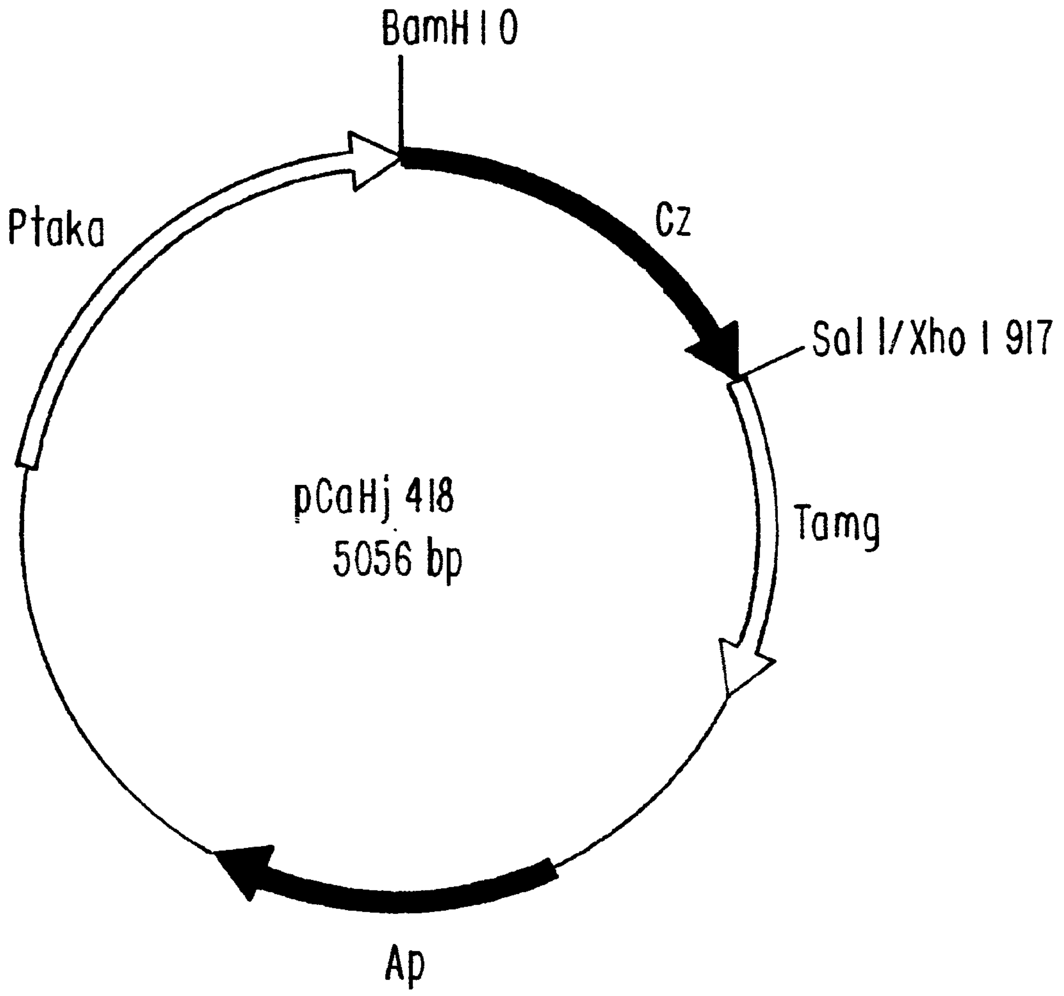

FIG. 10 shows a restriction map of pCaHj418.

Figure 11:
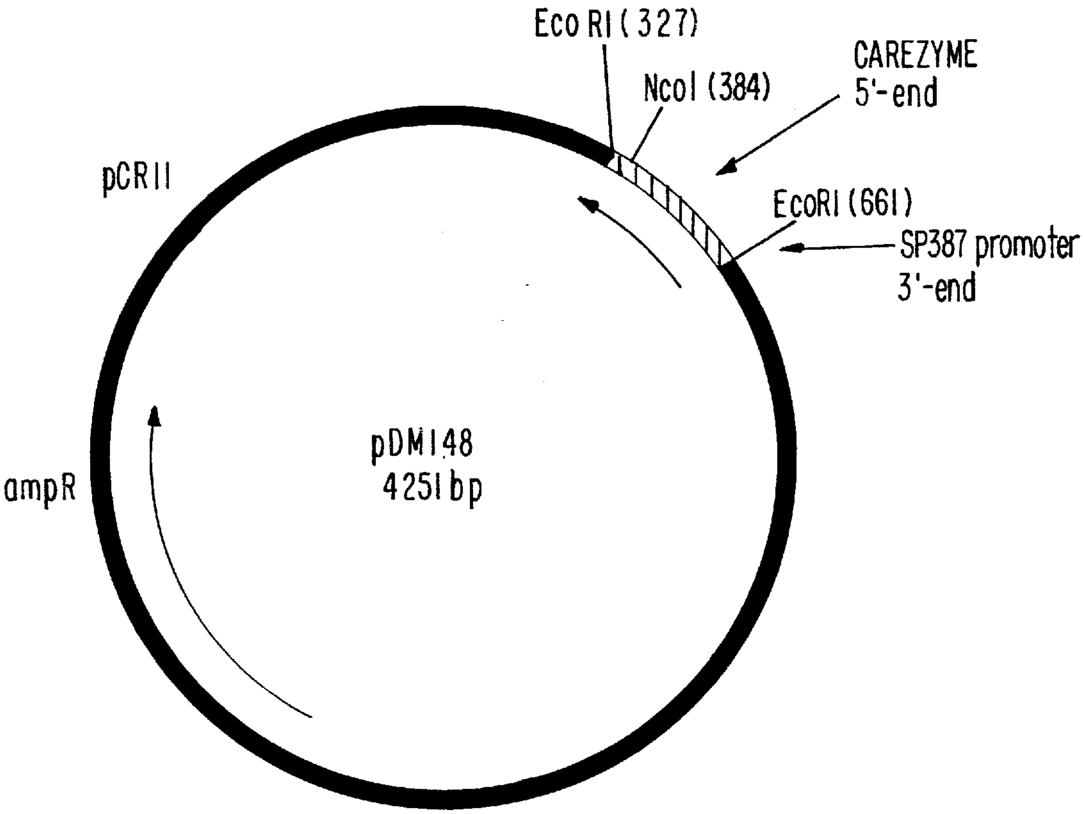

FIG. 11 shows a restriction map of pDM148.

Figure 12:
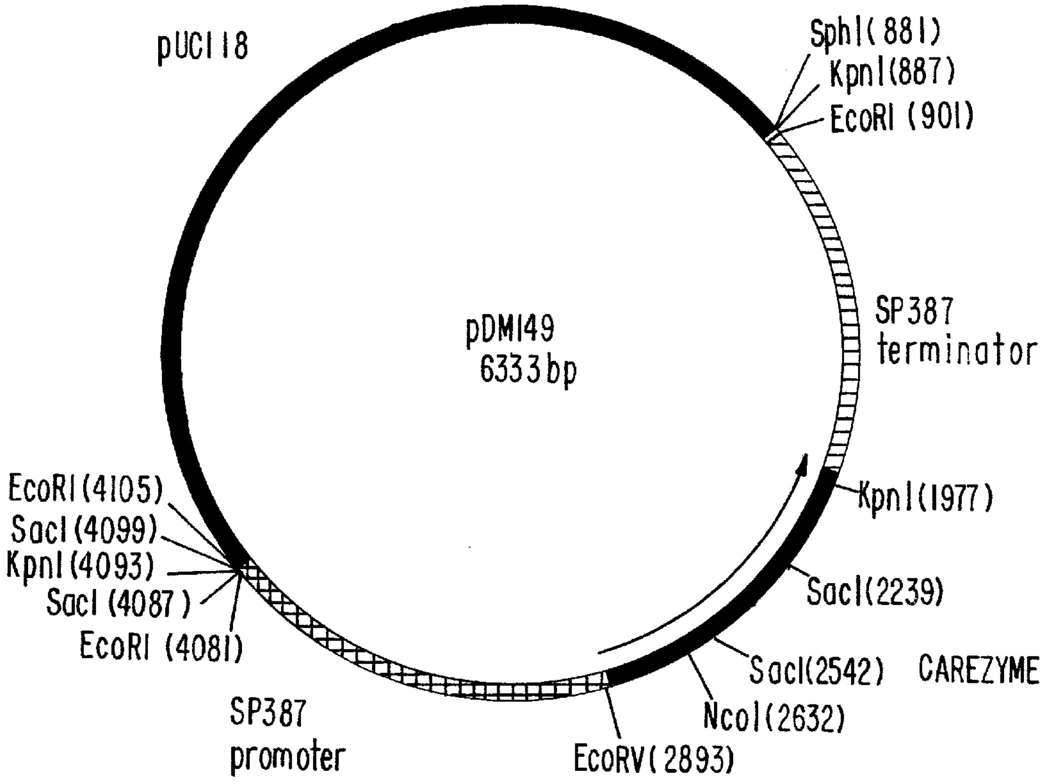

FIG. 12 shows a restriction map of pDM149.

Figure 13:
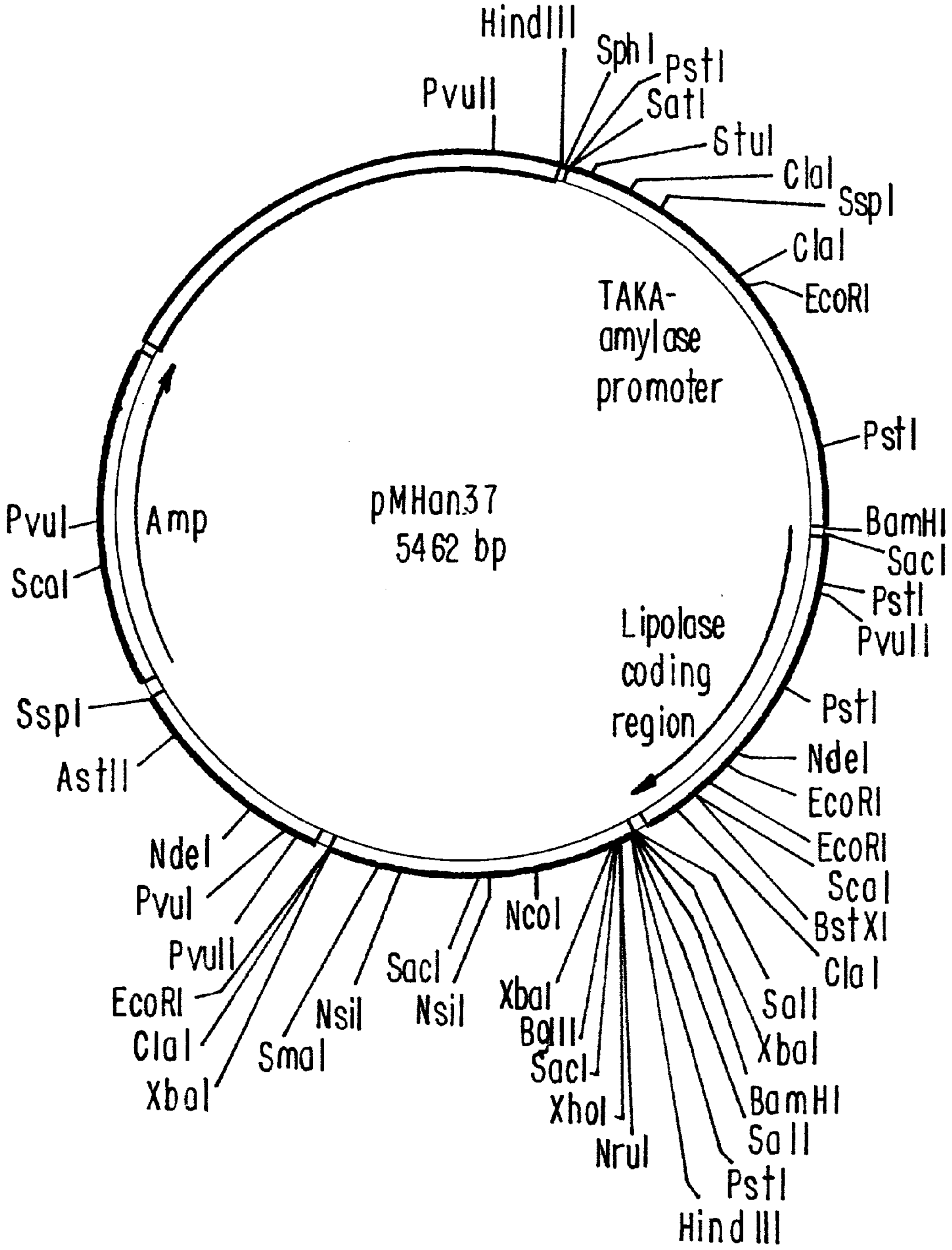

FIG. 13 shows a restriction map of pMHan37.

Figure 14:
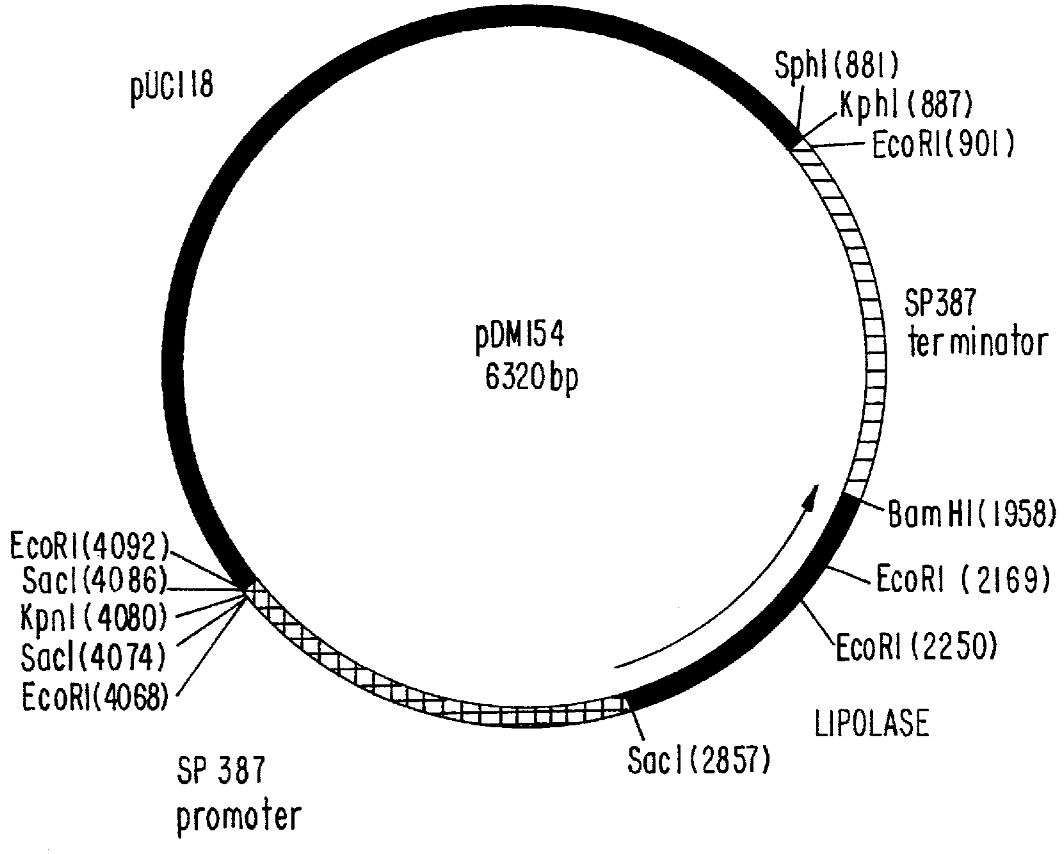

FIG. 14 shows a restriction map of pDM154.

DETAILED DESCRIPTION OF THE INVENTION

The present invention relates to non-toxic, non-toxigenic, non-pathogenic recombinant Fusarium host cell in the section Discolor (also known as the section Fusarium) or a synonym or teleomorph thereof, comprising a nucleic acid sequence encoding a heterologous protein operably linked to a promoter.

The known species in the section Discolor include, but are not limited to, *Fusarium bactridioides, Fusarium cerealis, Fusarium crookwellense, Fusarium culmorum, Fusarium graminearum, Fusarium graminum, Fusarium heterosporum, Fusarium negundi, Fusarium reticulatum, Fusarium roseum, Fusarium sambucinum, Fusarium sarcochroum, Fusarium sulphureum, Fusarium trichothecioides Fusarium venenatum*, most specifically, *Fusarium venatum* Nirenberg sp. nov., and *Fusarium toruloseum*. Known teleomorphs of Fusarium of the section Discolor include, but are not limited to, *Gibberella gordonii, Gibberella cyanea, Gibberella pulicaris*, and *Gibberella zeae*.

Fusarium strains are characterized by mycelium extensive and cotton-like in culture, often with some tinge of pink, purple or yellow in the mycelium on solid medium. Conidiophores are variable slender and simple, or stout, short, branched irregularly or bearing a whorl of phialides, single or grouped into sporodochia. Conidia are principally of two kinds, often held in small moist heads: macroconidia several-celled, slightly curved or bent at the pointed ends, typically canoe-shaped and microconidia which are one celled, ovoid or oblong, borne singly or in chains. Some conidia are intermediate, 2 or 3 celled, oblong or slightly curved.

As defined herein, "non-toxic" means that the host cell does not act as a poison to plants or animals. For example, a Fusarium host cell would be considered non-toxic if about 14 days after injecting about 5 mice with a dose of about 20 ml of (1:1 diluted) 3 day old Fusarium culture medium/kg body wt./mouse, none of the mice died as a result of Fusarium treatment. As defamed herein, "non-toxigenic" means that the host cells are essentially free of mycotoxin as determined by standard analytical methods such as HPLC analysis. For example, an amount of Fusarium grown on 2×9 cm petri dishes containing solid nutrient medium may be extracted with organic solvents and 0.5% of the extract may be injected into an HPLC for analysis. The absence of known mycotoxins would be inferred by the absence of detectable HPLC peaks at positions known for mycotoxin standards. As defined herein, "non-pathogenic" means that the host cells do not cause significant disease in healthy plants or healthy animals. For example, a Fusarium sp. that is pathogenic to plants can show a fungal invasion of the xylem tissue of the plant and result in the disease state characterized by typical wilt symptoms. As defined herein, a "heterologous protein" is a protein which is not native to the host cell, or a native protein in which modifications have been made to alter the native sequence or a native protein whose expression is quantitatively altered as a result of a manipulation of a native regulatory sequence required for the expression of the native protein, such as a promoter, a ribosome binding site, etc. or other manipulation of the host cell by recombinant DNA techniques. The nucleic acid sequence is operably linked to a suitable promoter sequence, which is capable of directing transcription of the nucleic acid sequence in the chosen host cell.

In a specific embodiment, the host cells of the present invention are of the species *Fusarium graminearum* which is characterized by the following features. Conidia: Microconidia are absent. Macroconidia are distinctly septate, thick walled, straight to moderately sickle-shaped, unequally curved with the ventral surface almost straight and a smoothly arched dorsal surface. The basal cell is distinctly foot-shaped. The apical cell is cone-shaped or constricted as a snout. Conidiophores: unbranched and branched monophialides. Chlamydospores: are generally very slow to form in culture: when they do occur, they most often form in the macroconidia but may also form in the mycelium. Colony morphology: on PDA, growth is rapid with dense aerial mycelium that may almost fill the tube and is frequently yellow to tan with the margins white to carmine red. Red-brown to orange sporodochia, if present, are sparse, often appearing only when the cultures are more than 30 days old. The undersurface is usually carmine red. This fungus produces the most cylindrical (dorsal and ventral surfaces parallel) macroconidia of any species of the section Discolor.

In a most specific embodiment, the Fusarium strain has been deposited with the American Type Culture Collection and assigned the number ATCC 20334 and has been identified as *Fusarium graminearum* Schwabe IMI 145425 in U.S. Pat. No. 4,041,189. The Fusarium strain may also be derivatives and mutants which are similarly non-toxic, non-toxigenic, and non-pathogenic, e.g. those taught in U.S. Pat. No. 4,041,189.

It will be understood that throughout the specification and claims the use of the term "*Fusarium graminearum*" refers not only to organisms encompassed in this species, but also includes those species which have previously been or currently are designated as other species in alternate classification schemes, but which possess the same morphological and cultural characteristics defamed above, and may be synonymous to *F. graminearum*. These include but are not limited to *Fusarium roseum, F. roseum* var. graminearum, *Gibberella zeae*, or *Gibberella roseum, Gibberella roseum* f. sp. *cerealis*.

The skilled artisan will also recognize that the successful transformation of the host species described herein is not limited to the use of the vectors, promoters, and selection markers specifically exemplified. Generally speaking, those techniques which are useful in transformation of *F. oxysporum, F. solani* and *F. culmorum* are also useful with the host cells of the present invention. For example, although the amdS selection marker is preferred, other useful selection markers include the argB (*A. nidulans* or *A. niger*), trpC (*A. niger* or *A. nidulans*), pyrG (*A. niger, A. oryzae* or *A. nidulans*), niaD (*A. nidulans, A. niger*, or *F. oxysporum*), and hygB (*E. coli*) markers. The promoter may be any DNA sequence that shows strong transcriptional activity in these species, and may be derived from genes encoding both extracellular and intracellular proteins, such as amylases, glucoamylases, proteases, lipases, cellulases and glycolytic enzymes. Examples of such promoters include but are not limited to *A. nidulans* amdS promoter or promoters from genes for glycolytic enzymes, e.g., TPI, ADH, GAPDH, and PGK. The promoter may also be a homologous promoter, i.e., the promoter for a gene native to the host strain being used. The promoter sequence may also be provided with linkers for the purpose of introducing specific restriction sites facilitating ligation of the promoter sequence with the gene of choice or with a selected signal peptide or preregion.

The promoter sequence may be derived from a gene encoding a *Fusarium oxysporum* trypsin-like protease or a fragment thereof having substantially the same promoter activity as said sequence. The sequence of the promoter is shown in SEQ ID NO:5. The invention further encompasses nucleic acid sequences which hybridize to the promoter sequence shown in SEQ ID NO:5 under the following conditions:presoaking in 5×SSC and prehybridizing for 1 hr. at about 40° C. in a solution of 20% formamide, 5×Denhardt's solution, 50 mM sodium phosphate, pH 6.8, and 50 ug denatured sonicated calf thymus DNA, followed by hybridization in the same solution supplemented with 100 uM ATP for 18 hrs. at about 40° C., followed by a wash in 0.4×SSC at a temperature of about 45° C., or which have at least about 90% homology and preferably about 95% homology to SEQ ID NO:5, but which have substantially the same promoter activity as said sequence. In another embodiment, the promoter may be a sequence comprising a large number of binding sites of AreA, a positive regulator of genes expressed during nitrogen limitation; these sites are referred to as nit-2 in *Neurospora crassa* (Fu and Marzlus, 1990, Proc. Natl. Acad. Sci. U.S.A. 87:5331–5335). The promoter sequence may be modified by the addition or substitution of such AreA sites.

Terminators and polyadenylation sequences may also be derived from the same sources as the promoters. In a specific embodiment, the terminator sequence may be derived from a gene encoding a *Fusarium oxysporum* trypsin-like protease or a fragment thereof having substantially the same terminator activity as said sequence. The sequence of the terminator is shown in SEQ ID NO:6. The invention further encompasses nucleic acid sequences which hybridize to the terminator sequence shown in SEQ ID NO:6 under the following conditions: presoaking in 5×SSC and prehybridizing for 1 hr. at about 40° C. in a solution of 20% formamide, 5×Denhardt's solution, 50 mM sodium phosphate, pH 6.8, and 50 ug denatured sonicated calf thymus DNA, followed by hybridization in the same solution supplemented with 100 uM ATP for 18 hrs. at about 40° C., followed by a wash in 0.4×SSC at a temperature of about 45° C., or which have at least about 90% homology and preferably about 95% homology to SEQ ID NO:5, but which have substantially the same terminator activity as said sequence.

Enhancer sequences may also be inserted into the construct.

To avoid the necessity of disrupting the cell to obtain the expressed product, and to minimize the amount of possible degradation of the expressed product within the cell, it is preferred that the product be secreted outside the cell. To this end, in a preferred embodiment, the gene of interest is linked to a preregion such as a signal or leader peptide which can direct the expressed product into the cell's secretory pathway. The preregion may be derived from genes for any secreted protein from any organism, or may be the native preregion. Among useful available sources for such a preregion are a glucoamylase or an amylase gene from an Aspergillus species, an amylase gene from a Bacillus species, a lipase or proteinase gene from *Rhizomucor miehei*, the gene for the alpha-factor from *Saccharomyces cerevisiae*, or the calf prochymosin gene. The preregion may be derived from the gene for *A. oryzae* TAKA amylase, *A. niger* neutral alpha-amylase, *A. niger* acid stable α-amylase, *B. licheniformis* α-amylase, the maltogenic amylase from Bacillus NCIB 11837, *B. stearothermophilus* α-amylase, or *B. licheniformis* subtilisin. An effective signal sequence is the *A. oryzae* TAKA amylase signal, the *Rhizomucor miehei* aspartic proteinase signal and the *Rhizomucor miehei* lipase signal. As an alternative, the preregion native to the gene being expressed may also be used, e.g., in SEQ ID NO:4 between amino acids −24 and −5.

The gene for the desired product functionally linked to promoter and terminator sequences may be incorporated in a vector containing the selection marker or may be placed on a separate vector or plasmid capable of being integrated into the genome of the host strain. Alternatively, the vectors used may be capable of replicating as linear or circular extrachromosomal elements in the host cell. These types of vectors include for example, plasmids and minichromosomes. The vector system may be a single vector or plasmid or two or more vectors or plasmids which together contain the total DNA to be integrated into the genome. Vectors or plasmids may be linear or closed circular molecules.

The host cell may be transformed with the nucleic acid encoding the heterologous protein using procedures known in the art such as transformation and electroporation (see, for example, Fincham, 1989, Microbial Rev. 53:148–170).

The recombinant host cell of the present invention may be cultured using procedures known in the art. Briefly, the host cells are cultured on standard growth medium such as those containing a combination of inorganic salts, vitamins, a suitable organic carbon source such as glucose or starch, any of a variety of complex nutrients sources (yeast extract, hydrolyzed casein, soya bean meal, etc.). One example is FP-1 medium (5% soya bean meal, 5% glucose, 2% $K_2HPO_4$, 0.2% $CaCl_2$, 0.2% $MgSO_47H_2O$ and 0.1% pluronic acid (BASF)). The fermentation is carried out at a pH of about 4.5–8.0, and at a temperature of about 20–37° C. for about 2–7 days.

The present host cell species can be used to express any prokaryotic or eukaryotic heterologous protein of interest, and is preferably used to express eukaryotic proteins. Of particular interest for these species is their use in expression of heterologous proteins, especially fungal enzymes. The novel expression systems can be used to express enzymes such as catalase, laccase, phenoloxidase, oxidase, oxidoreductases, cellulase, xylanase, peroxidase, lipase, hydrolase, esterase, cutinase, protease and other proteolytic enzymes, aminopeptidase, carboxypeptidase, phytase, lyase, pectinase and other pectinolytic enzymes, amylase, glucoamylase, alpha-galactosidase, β-galactosidase, α-glucosidase, β-glucosidase, mannosidase, isomerase, invertase, transferase, ribonuclease, chitinase, mutanase and deoxyribonuclease.

In a specific embodiment, the enzyme is an alkaline protease, e.g., a *Fusarium oxysporum* pre-pro-trypsin gene. In a most specific embodiment, the genomic sequence is shown in SEQ ID NO:3 and the protein sequence is shown in SEQ ID NO:4.

In another specific embodiment, the enzyme is an alkaline endoglucanase, which is immunologically reactive with an antibody raised against a highly purified ~43 kD endoglucanase derived from *Humicola insolens*, DSM 1800, or which is a derivative of the ~43 kD endoglucanase exhibiting cellulase activity (cf. WO 91/17243). The endoglucanase, hereinafter referred to as "CAREZYME®" may be encoded by a gene shown in SEQ ID NO:7 and may have a protein sequence shown in SEQ ID NO:8. The enzyme may also be a CAREZYME® variant.

In yet another specific embodiment, the enzyme is a 1,3-specific lipase, hereinafter referred to as LIPOLASE®. The enzyme may be encoded by the DNA sequence shown in SEQ ID NO:9 and may have an amino acid sequence shown in SEQ ID NO:10. The enzyme may also be a LIPOLASE® variant, e.g., D96L, E210K, E210L (see WO 92/05249).

It will be understood by those skilled in the art that the term "fungal enzymes" includes not only native fungal enzymes, but also those fungal enzymes which have been modified by amino acid substitutions, deletions, additions, or other modifications which may be made to enhance activity, thermostability, pH tolerance and the like. The present host cell species can also be used to express heterologous proteins of pharmaceutical interest such as hormones, growth factors, receptors, and the like.

The present invention will be further illustrated by the following non-limiting examples.

EXAMPLES

Example 1

*Fusarium graminearum* ATCC 20334 Secretes Only a Low Level of Protein

Figure 1:
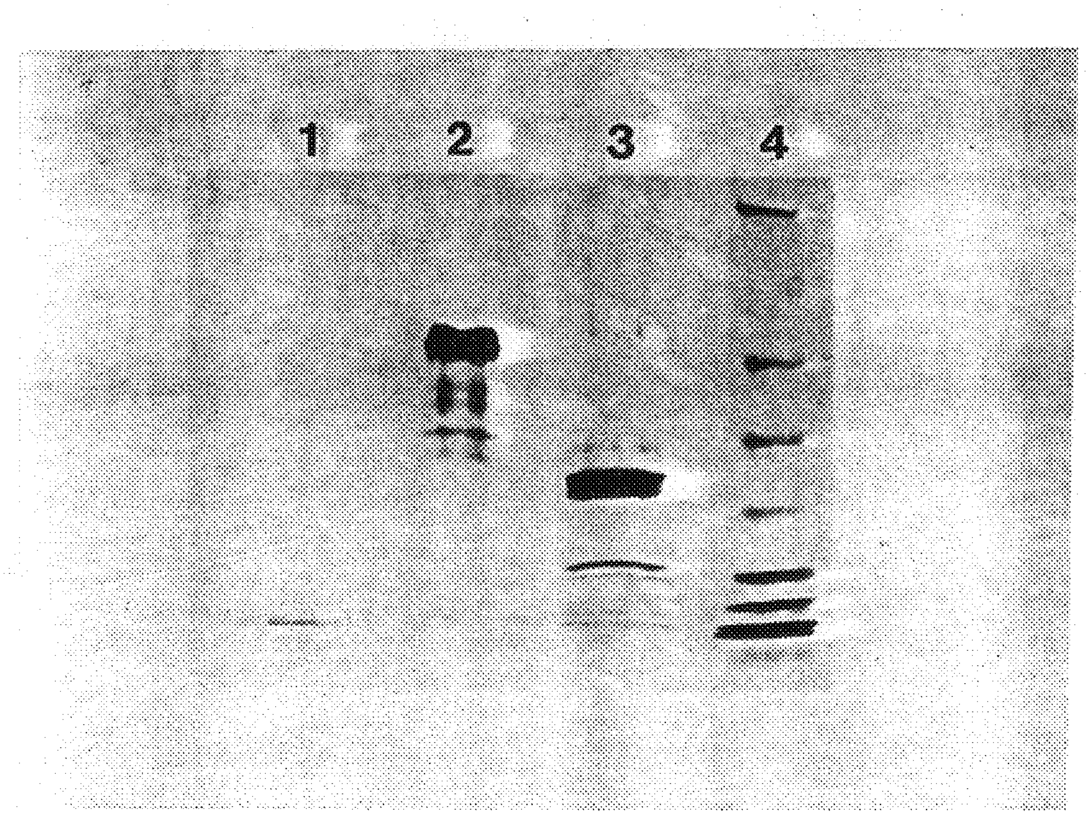
FIG. 1 shows an SDS-PAGE gel of secreted proteins in *Fusarium graminearum* (lane 1); *Aspergillus niger* (lane 2); and *Aspergillus oryzae* (lane 3). Lane 4 shows molecular weight markers.

Conidial spore suspensions of *Fusarium graminearum* strain ATCC 20334, an *A. oryzae*, and *A. niger* are inoculated into 25 ml of YPD medium (1% yeast extract (Difco), 2% bactopeptone (Difco), 2% glucose) in a 125 ml shake flask and incubated at 30° C. at 300 rpm for 5 days. Supernatant broths from the cultures are harvested by centrifugation. A total of 10 μl of each sample are mixed with 10 μl 0.1 M dithiothreitol (Sigma) and 10 μl of loading buffer (40 mM Tris base, 6% sodium dodecyl sulfate, 2.5 mM EDTA, 15% glycerol, 2 mg/ml bromocresol purple). The samples are boiled for 5 minutes and run on a 4–12% polyacrylamide gel (Novex). The proteins are visualized by staining with Coomassie Blue. The results (FIG. 1) show that *Fusarium graminearum* strain ATCC 20334 produces very little secreted protein.

Example 2

*Fusarium graminearum* ATCC 20334 Secretes Only a Low Level of Proteases

Figure 2:
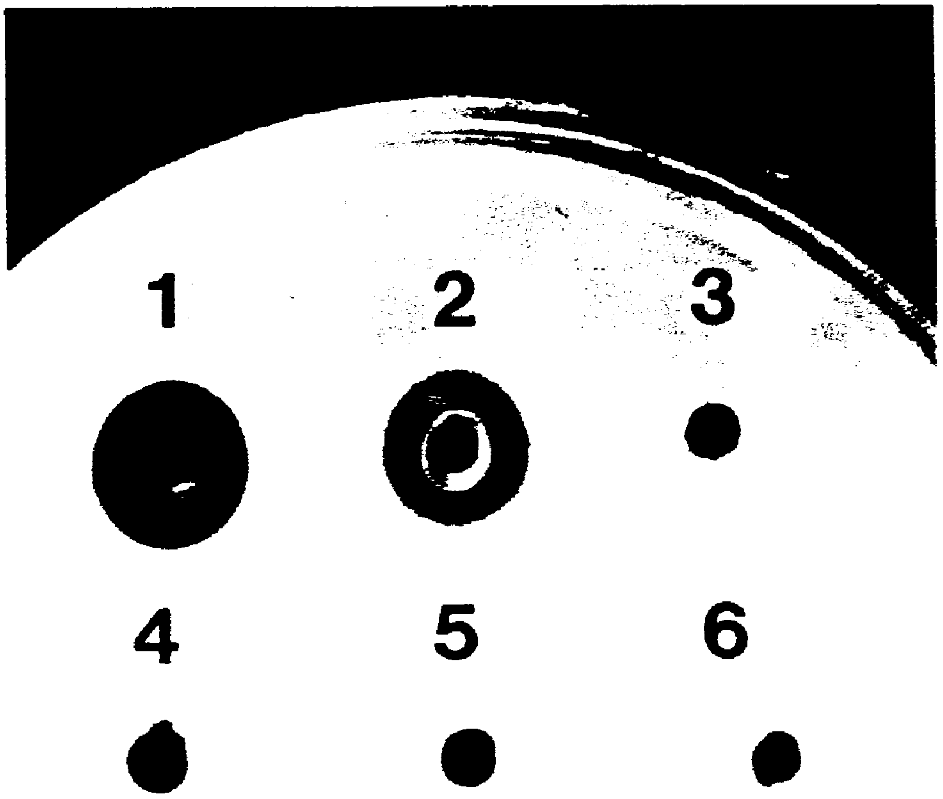
FIG. 2 shows the results of a protease assay on the following samples: *Aspergillus oryzae* (well 1); *Aspergillus niger* (well 2); *Fusarium graminearum* (well 3); empty well controls (wells 4–6).

A total of 40 μl of culture broths from *Fusarium graminearum* strain ATCC 20334, *A. oryzae*, and *A. niger* (see Example 1) are each pipetted into wells that are cut into a casein agar plate (2% non-fat dry milk (Lucerne), 50 mM Tris-HCl pH=7.5, 1% noble agar (Difco)). The plates are incubated at 37° C. for 5 hours and the zones of protein hydrolysis are observed. The results (FIG. 2) show that *Fusarium graminearum* strain ATCC 20334 broth contains very little proteolytic activity.

Example 3

Cloning of *Fusarium oxysporum* Genomic Prepro-trypsin Gene

A genomic DNA library in lambda phage is prepared from the *F. oxysporum* genomic DNA using methods such as those described found in Sambrook et al., 1989, Molecular Cloning, A Laboratory Manual, Cold Spring Harbor, N.Y. A total of 50 μg genomic DNA are digested in a volume of 200 μl containing 10 mM Tris (pH=7.5), 50 mM NaCl, 7 mM $MgCl_2$, 7 mM 2-mercaptoethanol, and 4 units restriction enzyme Sau3A for one minute at 37° C. Partially digested DNA of molecular size 10–20 kb is isolated by agarose gel electrophoresis, followed by electroelution into dialysis membrane and concentration using an Elutip-D column (Schleicher and Schuell). One μg of lambda arms of phage of EMBL4 that had been cut with restriction enzyme BamH1 and treated with phosphatase (Clonetech) is ligated with 300–400 μg Sau3A cut genomic DNA in a volume of 25 μl under standard conditions (see Sambrook et al., 1989, Molecular Cloning, A Laboratory Manual, Cold Spring Harbor, N.Y.). Lambda phage are prepared from this ligation mix using a commercially available kit (Gigapack Gold II, Stratagene) following the manufacturers directions.

The plating of ca. 15,000 recombinant lambda phage and the production of filter lifts (to Hybond $N^+$ filters, Amersham) are performed using standard methods (Sambrook et al., 1989, Molecular Cloning, A Laboratory Manual, Cold Spring Harbor, N.Y.). The filters are processed for hybridization with a Genius Kit for nonradioactive nucleic acids detection (Boehringer Mannheim) using standard methods (Sambrook et al., 1989, Molecular Cloning, A Laboratory Manual, Cold Spring Harbor, N.Y.). The DNA used as a probe is a 0.75 kb digoxygenin (DIG) labeled PCR fragment of the entire coding region of the *F. oxysporum* trypsin-like protease (hereinafter referred to as SP387) gene present in plasmid pSX233, which has been deposited with the NRRL under the accession number of NRRL B-21241. The primers for the PCR reaction are 5'-tgcggatccATGGTCAAGTTCGCTTCCGTC (forward primer; SEQ ID NO:1) and 5'-gacctcgagTTAAGCATAGGTGTCAATGAA (reverse primer; SEQ ID NO:2). In both primers, the lower case characters represent linker sequences and the upper case characters correspond to the coding region of the SP387 gene. To perform the PCR, 25 ng of a 907 bp BamH1/Xba1 DNA fragment containing the SP387 gene from plasmid pSX233 are mixed with 68 pmoles of each forward and reverse priner.

The mixture of the DNA fragment and primers is made up to an 80 μl volume in 1×Taq Buffer/1×DIG labelling Mix/5 units Taq (Boehringer Mannheim). The reaction conditions are 95° C., 3 minutes, then 35 cycles of [95° C. 30 seconds, 50° C. 1 minute, 72° C. 1 minute]. The DNA sequence derived by PCR from the *F. oxysporum* trypsin-like protease is shown in SEQ ID NO:3. The phage plaques are screened with the DIG labeled probe using a modification (Engler and Blum, 1993, Anal. Biochem. 210:235–244) of the Genius kit (Boehringer Mannheim). Positive clones are isolated and purified by a second round of plating and hybridization. Recombinant lambda phage containing the *F. oxysporum* trypsin-like protease gene are prepared and DNA is isolated from the phage using a Quiagen lambda midi preparation kit (Quiagen).

Example 4

Construction of Expression Plasmid pJRoy6

Figure 3:
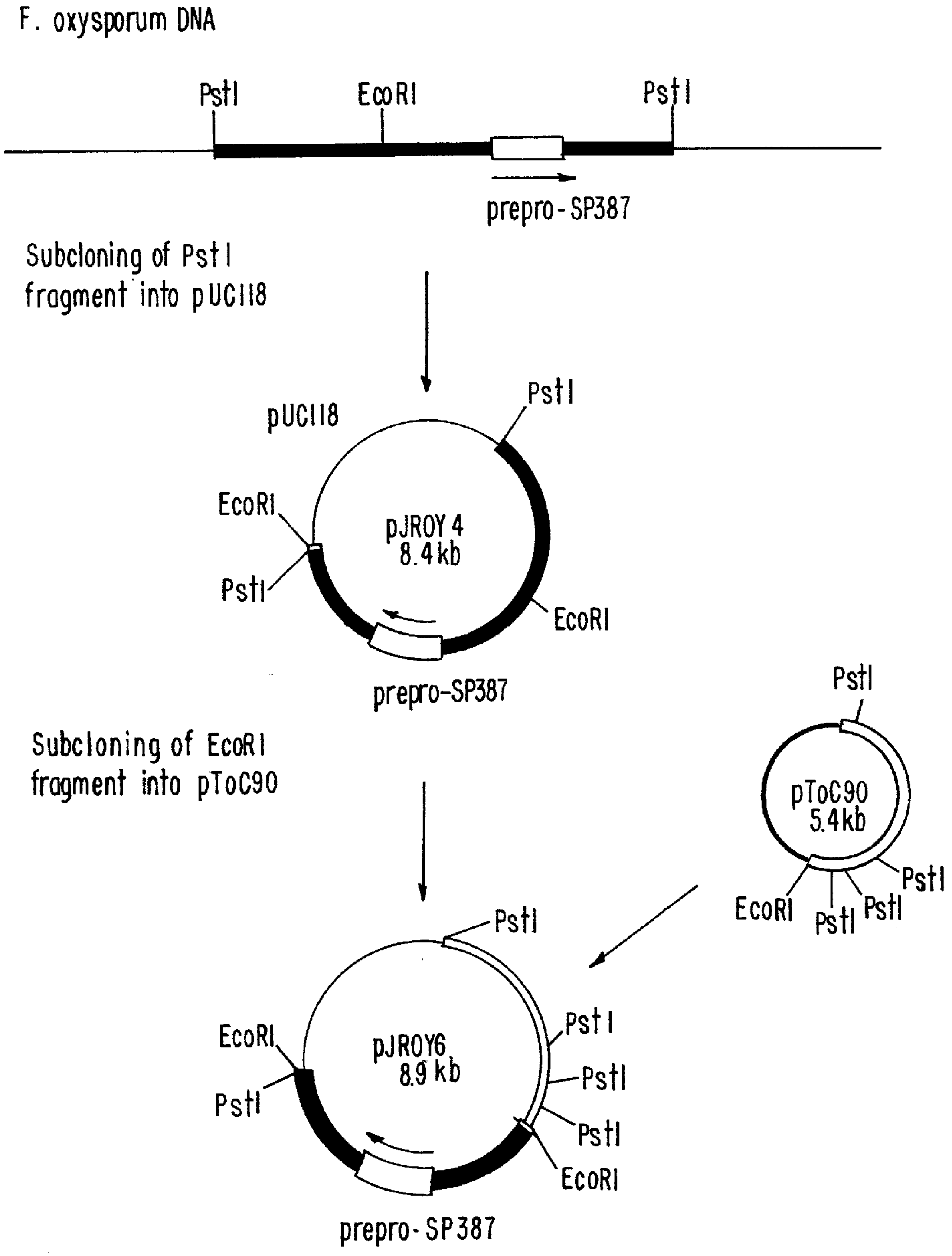
FIG. 3 shows the construction of plasmid pJRoy6.
Figure 4:
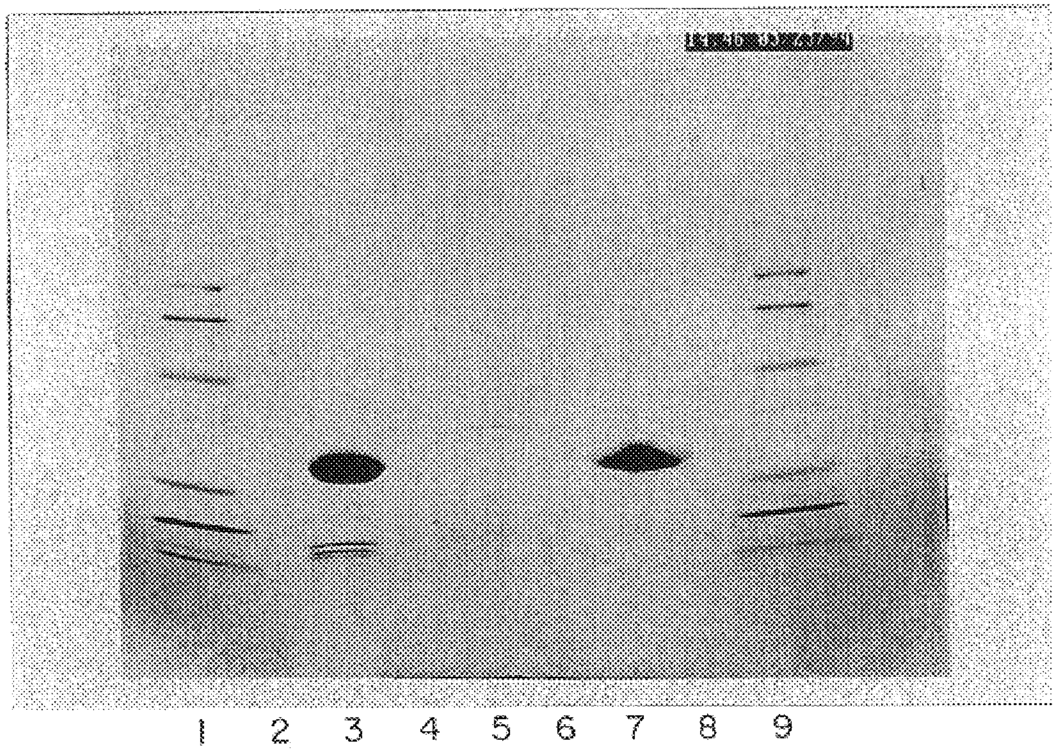
FIG. 4 shows SDS-PAGE analysis of the secretion of a trypsin-like protease (SP387) in a transformant of *F. graminearum* ATCC 20334. Lane 1: molecular size markers; lane 2: blank; lane 3: purified trypsin-like protease protein standard; lane 4: blank; lane 5*: F. graminearum* strain ATCC 20334 untransformed; lane 6: blank; lane 7*: F. graminearum* strain ATCC 20334 transformed with plasmid pJRoy6; lane 8: blank; line 9: molecular size markers.

Restriction mapping, Southern blotting, and hybridization techniques (Sambrook et al., 1989, Molecular Cloning, A Laboratory Manual, Cold Spring Harbor, N.Y.) are used to identify a 5.5 kb Pst1 restriction enzyme fragment from one of the recombinant phage that contains the *F. oxysporum* trypsin-like protease coding gene and flanking DNA sequences. This 5.5 kb Pst1 fragment is subcloned into Pst1 digested pUC118 and the plasmid is designated pJRoy4 (see FIG. 3). Plasmid pJRoy4 is digested with restriction enzyme EcoR1 and a 3.5 kb EcoR1 fragment containing the SP387 gene and the 43 bp EcoR1/Pst1 region of the pUC118 polylinker is isolated and subcloned into the vector pToC90 to create plasmid pJRoy6 (FIG. 3).

Example 5

Construction of SP387 Expression Cassette

Figure 5:
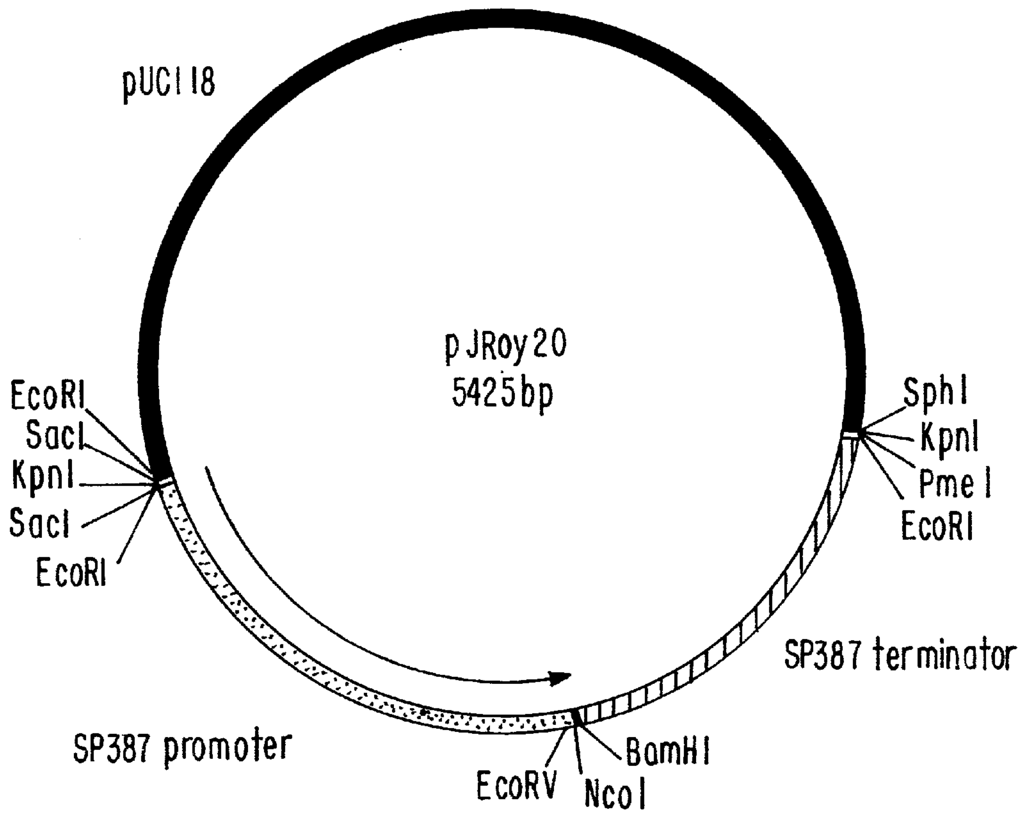
FIG. 5 shows a restriction map of pJRoy20.

An expression cassette (pJRoy20) containing the SP387 promoter and terminator joined by a BamH1 site in pUC118 is constructed. An *E. coli* strain containing pJRoy20 has been deposited with the NRRL. The promoter fragment is generated by digesting the SP387 vector pJRoy6 with EcoR1 (which cuts at −1200) and with Nco1 (which cuts at the translational start site, see FIG. 5). The terminator sequence (bp 2056–3107 in FIG. 5) is generated by PCR amplification using the following oligonucleotides:

FORWARD

5'gcacaccatggtcgctggatccATACCT-TGTTGGAAGCGTCG3' (SEQ ID NO:11)

REVERSE

5'atcggagcatgcggtaccgtttaaac-gaattcAGGTAAACAAGATATAATTTTCTG3' (SEQ ID NO:12)

Letters in large case are complementary to SP387 terminator DNA, while lower case letters are tails containing engineered restriction sites.

After digestion with Nco1 and Sph1, the resulting amplification product containing the terminator flanked by Nco1 and BamH1 sites on the 5' end, and flanked by EcoR1, Pme1, Kpn1 and Sph1 sites on the 3' end is isolated. A 3-way ligation between the promoter fragment, the terminator fragment and Kpn1/Sph1 cut pUC118 is performed to generate pJRoy20 (see FIG. 5).

Example 6

CAREZYME® Constructs

The EcoRV site at −15 in the SP387 promoter, and the Nco1 site present at +243 in the CAREZYME® coding region are utilized to create an exact fusion between the SP387 promoter and the CAREZYME® gene. A PCR fragment containing −18 to −1 of the SP387 promoter directly followed by −1 to +294 of the CAREZYME® gene is generated from the CAREZYME® vector pCaHj418 (see FIG. 10) using the following primers:

FORWARD

EcoRV

5'ctcttggatatctatctcttcaccAT-GCGTTCCTCCCCCCTCCT3' (SEQ ID NO:13)

REVERSE

5' CAATAGAGGTGGCAGCAAAA 3' (SEQ ID NO:14)

Lower case letters in the forward primer ar bp −24 to −1 of the SP387 promoter, while upper case letters are bp 1 to 20 of CAREZYME®.

Figure 6:
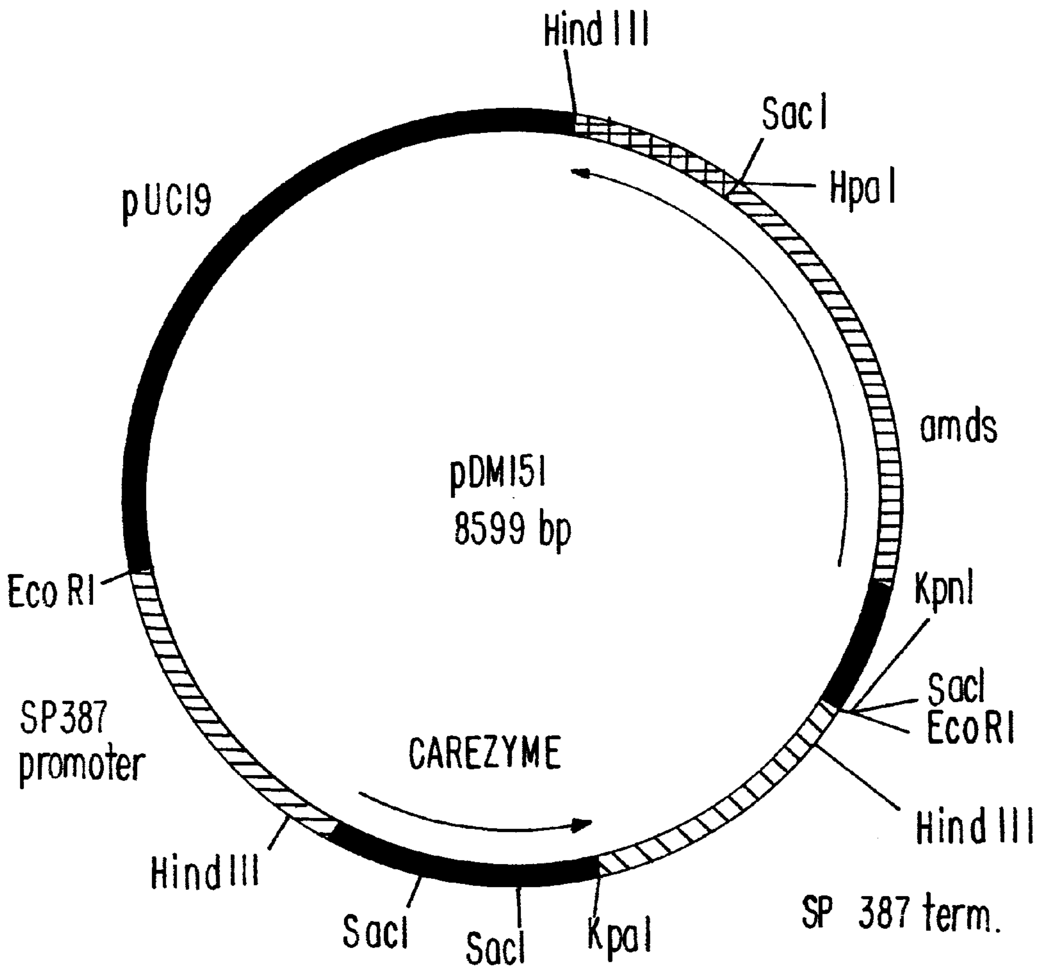
FIG. 6 shows a restriction map of pDM151.

The PCR conditions used are:95° C., 5 min. followed by 30 cycles of [95° C., 30 sec., 50° C., 1 min., 72° C., 1 min.]. The resulting 0.32 kb fragment is cloned into vector pCRII using Invitrogen's TA cloning kit resulting in pDM148 (see FIG. 11). The 0.26 kb EcoRV/NcoI fragment is isolated from pDM148 and ligated to the 0.69 kb NcoI/BglII fragment from pCaHj418 and cloned into EcoRV/BamHI digested pJRoy20 to create pDM149 (see FIG. 12). The 3.2 kb EcoRI CAREZYME® expression cassette (SP387 promoter/CAREZYME®/SP387 terminator) is isolated from pDM149 and cloned into the EcoRI site of pToC90 to create pDM151 (see FIG. 6). Expression construct pDM151 contains both the expression cassette and the amdS selectable marker. An *E. coli* strain containing pDM151 has been deposited with the NRRL.

Example 7

LIPOLASE® Constructs

The EcoRV site at −15 in the SP387 promoter, and the Sac1 site at +6 in the LIPOLASE® coding region are utilized to create an exact fusion between the SP387 promoter and the LIPOLASE® gene. An adapter containing the final 15 bp of the SP387 promoter followed by the first 6 bp of the LIPOLASE® coding region is constructed and is shown below.

| EcoRV | SacI |
|---|---|
| atctatctcttcaccATGAGGAGCT | (SEQ ID NO:15) |
| tagatagagaagtggTACTCC | (SEQ ID NO:16) |

Figure 7:
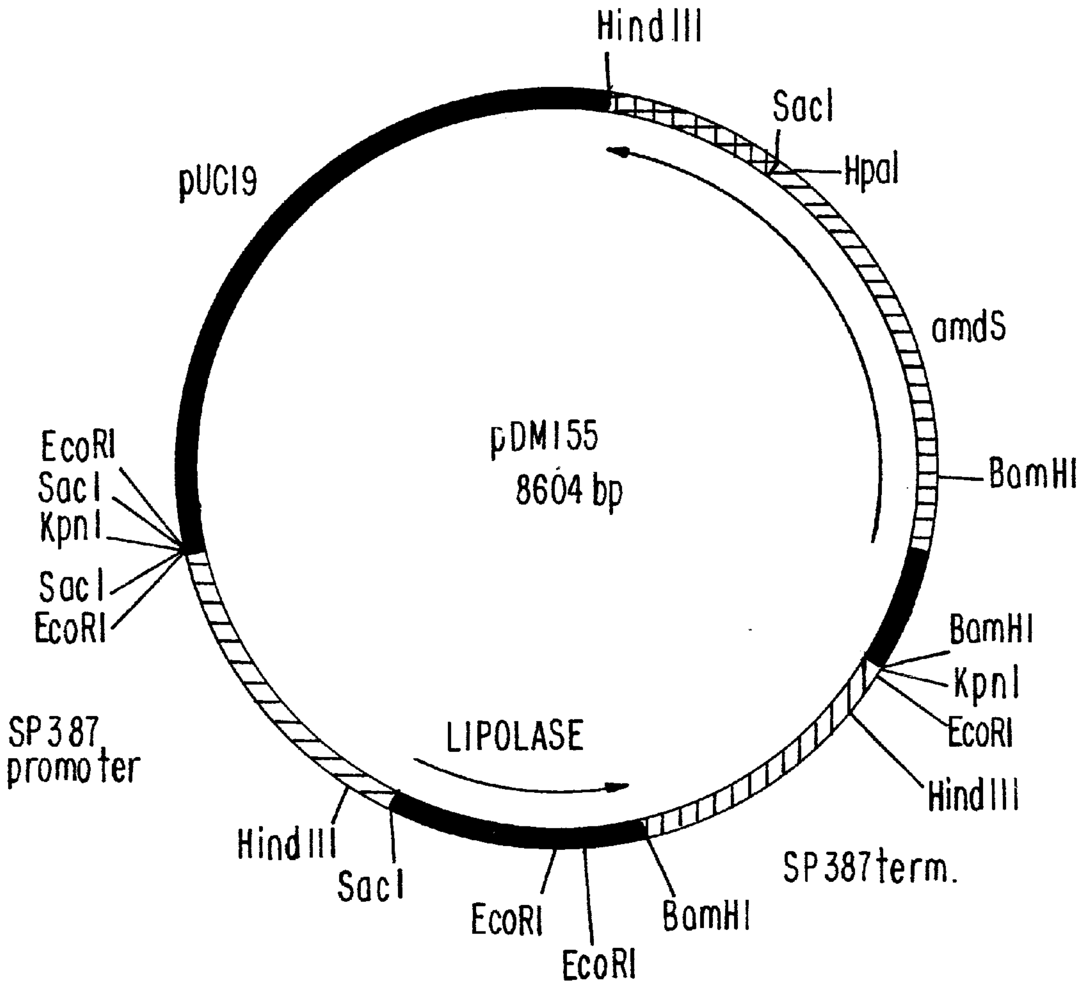
FIG. 7 shows a restriction map of pDM155.

A 0.9 kb SacI/BamHI fragment of the LIPOLASE® cDNA gene is isolated from the *A. oryzae* expression construct pMHan37 (see FIG. 13). The EcoRV/SacI adapter and SacI/BamHI LIPOLASE® fragment are ligated and cloned into EcoRV/BamHI digested pJRoy20 to create plasmid pDM154 (see FIG. 14). The 3.2 kb KpnI LIPOLASE® expression cassette (SP387 promoter/LIPOLASE®/SP387 terminator) is isolated from pDM154 and cloned into the KpnI site of pToC90 to create plasmid pDM155 (see FIG. 7). Expression construct pDM155 contains both the LIPOLASE® expression cassette and the amdS selectable marker. An *E. coli* strain containing pDM151 has been deposited with the NRRL.

Example 8

Transformation of *F. graminearum*

*Fusarium graminearum* strain ATCC 20334 cultures are grown on 100×15 mm petri plates of Vogels medium (Vogel, 1964, Am. Nature 98:435–446) plus 1.5% glucose and 1.5% agar for 3 weeks at 25° C. Conidia (approximately $10^8$ per plate) are dislodged in 10 ml of sterile water using a transfer loop and purified by filtration through 4 layers of cheesecloth and finally through one layer of miracloth. Conidial suspensions are concentrated by centrifugation. Fifty ml of YPG (1% yeast extract (Difco) 2% bactopeptone (Difco), 2% glucose) are inoculated with $10^8$ conidia, and incubated for 14 h at 20° C., 150 rpm. Resulting hyphae are trapped on a sterile 0.4 $\mu$m filter and washed successively with sterile distilled water and 1.0 M $MgSO_4$. The hyphae are resuspended in 10 ml of Novozym® 234 (Novo Nordisk) solution (2–10 mg/ml in 1.0 M $MgSO_4$) and digested for 15–30 min at 34° C. with agitation at 80 rpm. Undigested hyphal material is removed from the resulting protoplast suspension by successive filtration through 4 layers of cheesecloth and through miracloth. Twenty ml of 1M sorbitol are passed through the cheesecloth and miracloth and combined with the protoplast solution. After mixing, protoplasts (approximately $5\times10^8$) are pelleted by centrifugation and washed successively by resuspension and centrifugation in 20 ml of 1M sorbitol and in 20 ml of STC (0.8 m sorbitol, 50 mM Tris-HCl pH=8.0, 50 mM $CaCl_2$). The washed protoplasts are resuspended in 4 parts STC and 1 part SPTC (0.8M sorbitol, 40% polyethylene glycol 4000 (BDH), 50 mM Tris-HCl pH=8.0, 50 mM $CaCl_2$) at a concentration of $1–2\times10^8$/ml. One hundred $\mu$l of protoplast suspension are added to 5 $\mu$g pJRoy6 and 5 $\mu$l heparin (5 mg/ml in STC) in polypropylene tubes (17×100 mm) and incubated on ice for 30 min. One ml of SPTC is mixed gently into the protoplast suspension and incubation is continued at room temperature for 20 min. Protoplasts are plated on a selective medium consisting of Cove salts (Cove, D. J., 1966, Biochem. Biophys. Acta 113:51–56) plus 10 mM acetamide, 15 mM $CsCl_2$, 2.5% noble agar (Difco) and 1.0 M sucrose using an overlay of the same medium with 0.6 M sucrose and 1.0% low melting agarose (Sigma). Plates are incubated at 25° C. and transformants appeared in 6–21 days.

Example 9

Expression of Trypsin-like Protease in *Fusarium graminearum*

Transformants are transferred to plates of COVE2 medium (same as COVE medium above without the cesium chloride and replacing the 1.0 M sucrose with a concentration of 30 g/l) and grown for 3 or more days at 25° C. Twenty five ml aliquots of FP-1 medium (5% soya bean meal, 5% glucose 2% $K_2HPO_4$, 0.2% $CaCl_2$, 0.2% $MgSO_4.7H_2O$ and 0.1% pluronic acid (BASF)) in 150 ml flasks are inoculated with approximately 1 cm agar plugs from COVE2 plate cultures and incubated for 6 days at 30° C. with agitation (150 rpm). Supernatant broth samples are recovered after centrifugation and subjected to SDS-PAGE analysis as follows. Thirty μl of each broth is mixed with 10 μl SDS-PAGE sample buffer (1 ml 0.5 M Tris pH=6.8, 0.8 ml glycerol, 1.6 ml 10% SDS, 0.4 ml 0.8 M dithiothreitol, 0.2 ml 1% bromophenol blue), 2 μl of 2% PMSF (Sigma) in isopropanol, and 2 μl glycerol. The samples are placed in a boiling water bath for 4 minutes and 40 μl of each are run on a 10–27% polyacrylamide gel (Novex). The gels are stained and destained with Coomassie dye using standard methods. The expression level of the trypsin-like protease has been determined to be ≧0.5 g/l.

Example 10

Enzyme Assays

A. CAREZYME®

Buffer: Sodium phosphate (50 mM, pH 7.0)

Substrate: AZCL-HE cellulose (Megazyme) at 2 mg/ml buffer

Enzyme std: 100 mg of CAREZYME® standard (10,070 ECU/g) is dissolved in 1 ml buffer and stored at −20° C. This stock is diluted 1:100 in buffer immediately prior to use in enzyme assays. The assay range is 0.5–5.0 ECU/ml. A conversion factor of 650,000 ECU/g CAREZYME® is used.

Substrate solution (990 μl) is added to sample wells of a 24-well microtiter plate. Ten μl of CAREZYME® sample (diluted in buffer to produce activity of between 0.5 and 10 ECU/ml.) are added to the substrate. Reactions are incubated for 30 minutes at 45° C. with vigorous shaking, and next centrifuged at 4° C. for 5 minutes at 5,000 rpm. Two hundred μl of supernatant are transferred to a 96-well microtiter plate and the absorbance at 650 nm is measured.

B. LIPOLASE® Assay

Buffer: 0.1M MOPS, pH 7.5 containing 4 mM $CaCl_2$

Substrate: 10 mL p-nitrophenyl butyrate (pNB)

in 1 ml DMSO;

Add 4 ml buffer to substrate in DMSO

*Stock concentration=11.5 mM in 20% DMSO

Enzyme std: LIPOLASE® (23,100 LU/g) is dissolved at 1000 LU/ml in 50% glycerol and stored at −20° C. This stock is diluted 1:100 in buffer immediately prior to assay. The assay range is 0.125 to 3.0 LU/ml.

100 μl pNB stock solution is added to 100 μl of appropriately diluted enzyme sample. Activity (mOD/min) is measured at 405 nm for 5 min at 25° C.

C. SP387 Assay

L-BAPNA substrate is prepared by dilution of a 0.2 M stock solution of L-BAPNA (Sigma B3133) in dimethyl sulfoxide (stored frozen) to 0.004 M in buffer (0.01 M dimethylglutaric acid (Sigma), 0.2 M boric acid and 0.002 M calcium chloride, adjusted to pH 6.5 with NaOH) just prior to use. One μl of culture was centrifuged (145000×g, 10 min). A 100 μl aliquot of diluted culture broth is added to 100 μl substrate in a 96 well microtiter plate. Absorption change at 405 nm is assayed at 30 second intervals for 5 min. at 25° C. using an ELISA reader. Results are calculated relative to a purified SP387 standard.

Example 11

Expression of CAREZYME®

Figure 8A:
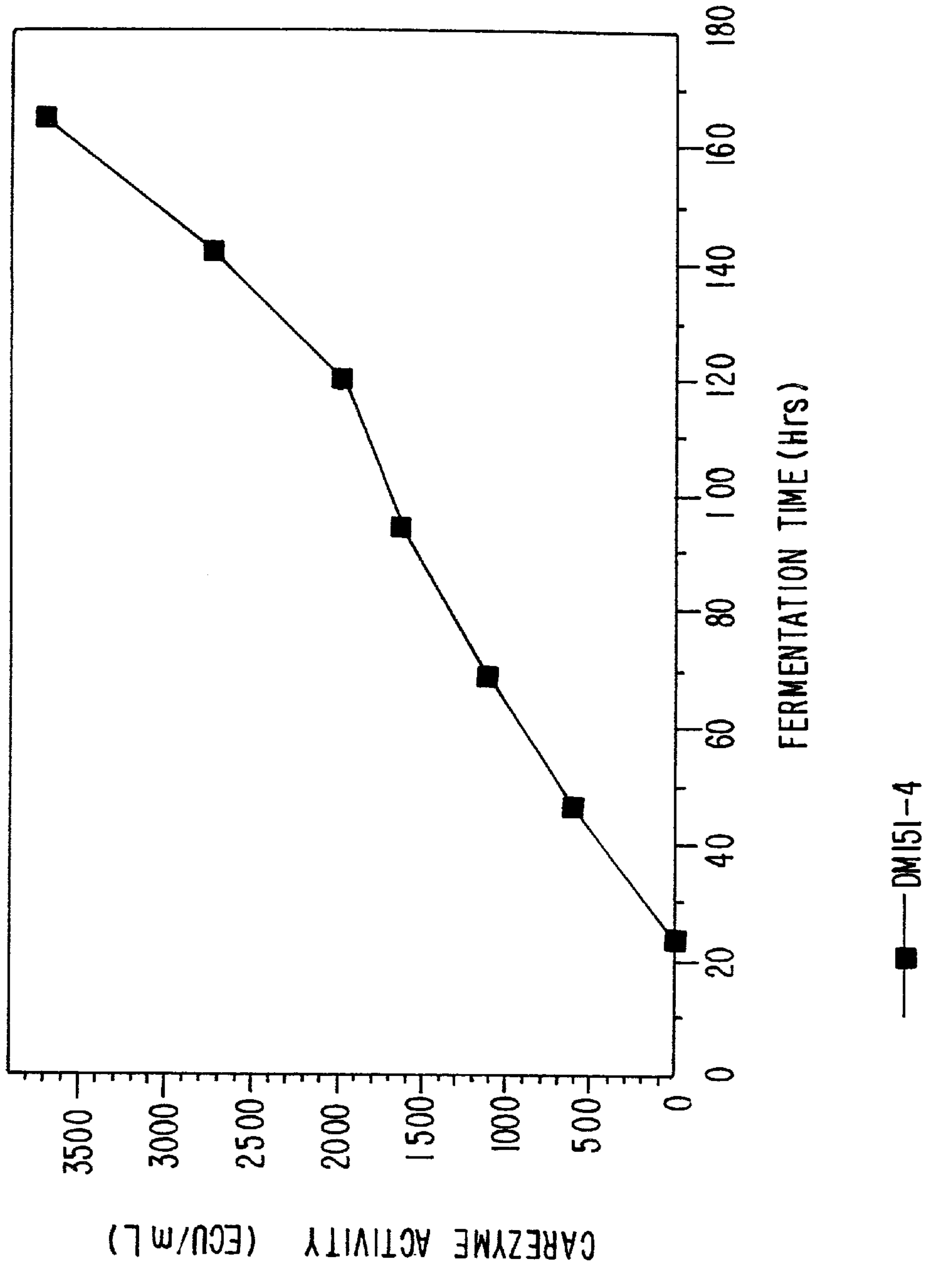
FIGS. 8A and 8B show the level of expression of CAREZYME® in *Fusarium graminearum* when DSM 151-4 is fermented in *Fusarium graminearum* from 20–160 hrs.
Figure 8B:
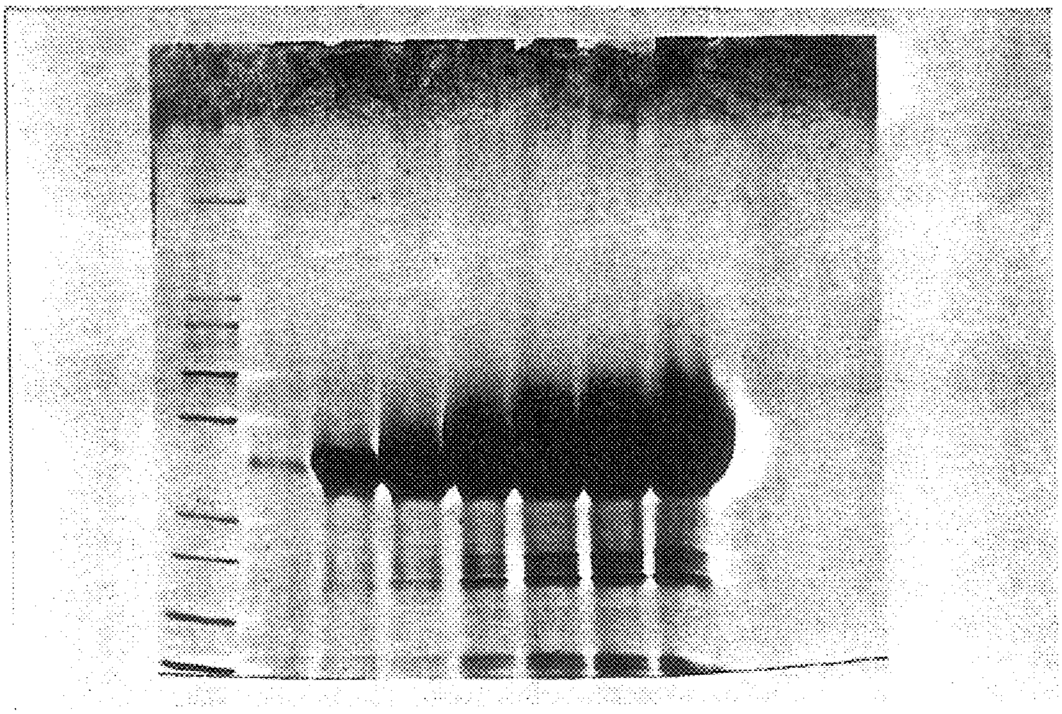

Twenty-three transformants of pDM151 are purified, cultured in shake flasks on soy/glucose medium and assayed for CAREZYME® activity after 9 days (Table 1-see below). Four transformants express CAREZYME® at a level of approximately 50–100 mg/L. Transformant pDM151-4 is cultured in small scale fermentors using the conditions developed for SP387 production (see Example 9). Approximately 6.0 g/L of CAREZYME® is evident after 7 days (FIG. 8A). CAREZYME® comprised greater than 90% of secreted proteins based on SDS gel electrophoresis (FIG. 8B).

TABLE I

| Transformant # | EMU/ml | mg/L |
|---|---|---|
| pDM 151.3-4 | 58.2 | 90 |
| pDM 151.3-5 | 0 | 0 |
| pDM 151.3-6 | 0 | 0 |
| pDM 151.3-10 | 0 | 0 |
| pDM 151.3-11 | 2.46 | 4 |
| pDM 151.3-12 | 0 | 0 |
| pDM 151.3-13 | 12.2 | 19 |
| pDM 151.3-14 | 47.3 | 73 |
| pDM 151.3-15 | 22.7 | 35 |
| pDM 151.3-16 | 0 | 0 |
| pDM 151.3-17 | 0 | 0 |
| pDM 151.3-18 | 0 | 0 |
| pDM 151.3-19 | 0 | 0 |
| pDM 151.3-21 | 0 | 0 |
| pDM 151.3-22 | 43.7 | 67 |
| pDM 151.3-23 | 1.25 | 2 |
| pDM 151.3-24 | 17.8 | 27 |
| pDM 151.3-25 | 38 | 58 |
| pDM 151.3-26 | 0 | 0 |
| pDM 151.3-27 | 10.5 | 16 |
| pDM 151.3-28 | 49.3 | 76 |
| pDM 151.3-29 | 19.8 | 30 |
| pDM 151.3-30 | 22.7 | 35 |

Example 12

Expression of LIPOLASE®

Fifteen transformants of pDM155 are purified, cultured in shake flasks in soy/glucose medium and assayed for LIPOLASE® activity after 9 days (Table 2-see next page).

TABLE II

| Transformant # | LU/ml | mg/ml |
|---|---|---|
| pDM 155-1 | 669 | 167 |
| pDM 155-2 | 45.2 | 11 |
| pDM 155-3 | 180 | 45 |

TABLE II-continued

| Transformant # | LU/ml | mg/ml |
|---|---|---|
| pDM 155-4 | 0 | 0 |
| pDM 155-5 | 55.4 | 14 |
| pDM 155-6 | 116 | 29 |
| pDM 155-7 | 704 | 176 |
| pDM 155-8 | 214 | 54 |
| pDM 155-9 | 17.1 | 4 |
| pDM 155-10 | 712 | 178 |
| pDM 155-11 | 511 | 128 |
| pDM 155-12 | 0 | 0 |
| pDM 155-13 | 0 | 0 |
| pDM 155-14 | 0 | 0 |
| pDM 155-15 | 153 | 38 |
| pDM 155-16 | 0 | 0 |
| pDM 155-17 | 0 | 0 |
| pDM 155-18 | 0 | 0 |
| pDM 155-19 | 129 | 32 |
| pDM 155-20 | 378 | 95 |
| pDM 155-21 | 216 | 54 |

Four transformants expressed LIPOLASE® at a level of approximately 100–200 mg/l (based on the pNB assay). Transformant pDM155-10 is cultured in small scale fermentors using the conditions developed for SP387 production (see Example 9). Approximately 2.0 g/l of LIPOLASE is evident after 7 days (FIG. 8A). LIPOLASE® comprised greater than 90% of secreted proteins based on SDS gel electrophoresis (FIG. 8B).

DEPOSIT OF MICROORGANISMS

The following biological materials have been deposited in the Agricultural Research Service Patent Culture Collection (NRRL), Northern Regional Research Center, 1815 University Street, Peoria, Ill., 61604, USA.

| Strain | Accession No. | Deposit Date |
|---|---|---|
| *E. coli* containing pJRoy6 | NRRL B-21285 | 6/20/94 |
| *E. coli* containing pJRoy20 | NRRL B-21418 | 3/10/95 |
| *E. coli* containing pDM151 | NRRL B-21419 | 3/10/95 |
| *E. coli* containing pDM155 | NRRL B-21420 | 3/10/95 |

The strains have been deposited under conditions that assure that access to the culture will be available during the pendency of this patent application to one determined by the Commissioner of Patents and Trademarks to be entitled thereto under 37 C.F.R. §1.14 and 35 U.S.C. §122 and under conditions of the Budapest Treaty. The deposit represents a biologically pure culture of each deposited strain. The deposit is available as required by foreign patent laws in countries wherein counterparts of the subject application, or its progeny are filed. However, it should be understood that the availability of a deposit does not constitute a license to practice the subject invention in derogation of patent rights granted by governmental action.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

Various references are cited herein, the disclosures of which are incorporated by reference in their entireties.

What is claimed is:

1. A non-toxic, non-toxigenic, non-pathogenic recombinant Fusarium host cell of the section Discolor having the identifying characteristics of ATCC 20334 which expresses a heterologous protein, comprising a nucleic acid sequence encoding said heterologous protein operably linked to a promoter.

* * * * *

UNITED STATES PATENT AND TRADEMARK OFFICE

CERTIFICATE OF CORRECTION

PATENT NO. : 6,060,305

DATED : May 9, 2000

INVENTOR(S) : Royer et al.

It is certified that error appears in the above-identified patent and that said Letters Patent is hereby corrected as shown below:

On the title page,

Section [75] Inventors

Delete-- Yoder T. Wendy--, Insert "Wendy T. Yoder"

Signed and Sealed this

Tenth Day of April, 2001

Attest:

Nicholas P. Godici

NICHOLAS P. GODICI

*Attesting Officer*

*Acting Director of the United States Patent and Trademark Office*

```
                         SEQUENCE LISTING


(1) GENERAL INFORMATION:

   (iii) NUMBER OF SEQUENCES: 16


(2) INFORMATION FOR SEQ ID NO:1:

     (i) SEQUENCE CHARACTERISTICS:
          (A) LENGTH: 30 base pairs
          (B) TYPE: nucleic acid
          (C) STRANDEDNESS: single
          (D) TOPOLOGY: linear

    (xi) SEQUENCE DESCRIPTION: SEQ ID NO:1:

TGCGGATCCA TGGTCAAGTT CGCTTCCGTC                                      30


(2) INFORMATION FOR SEQ ID NO:2:

     (i) SEQUENCE CHARACTERISTICS:
          (A) LENGTH: 30 base pairs
          (B) TYPE: nucleic acid
          (C) STRANDEDNESS: single
          (D) TOPOLOGY: linear

    (xi) SEQUENCE DESCRIPTION: SEQ ID NO:2:

GACCTCGAGT TAAGCATAGG TGTCAATGAA                                      30


(2) INFORMATION FOR SEQ ID NO:3:
```

-continued (i) SEQUENCE CHARACTERISTICS:
(A) LENGTH: 998 base pairs
(B) TYPE: nucleic acid
(C) STRANDEDNESS: single
(D) TOPOLOGY: linear (xi) SEQUENCE DESCRIPTION: SEQ ID NO:3:

```
ATCATCAACC ACTCTTCACT CTTCAACTCT CCTCTCTTGG ATATCTATCT CTTCACCATG     60

GTCAAGTTCG CTTCCGTCGT TGCACTTGTT GCTCCCCTGG CTGCTGCCGC TCCTCAGGAG    120

ATCCCCAACA TTGTTGGTGG CACTTCTGCC AGCGCTGGCG ACTTTCCCTT CATCGTGAGC    180

ATTAGCCGCA ACGGTGGCCC CTGGTGTGGA GGTTCTCTCC TCAACGCCAA CACCGTCTTG    240

ACTGCTGCCC ACTGCGTTTC CGGATACGCT CAGAGCGGTT TCCAGATTCG TGCTGGCAGT    300

CTGTCTCGCA CTTCTGGTGG TATTACCTCC TCGCTTTCCT CCGTCAGAGT TCACCCTAGC    360

TACAGCGGAA ACAACAACGA TCTTGCTATT CTGAAGCTCT CTACTTCCAT CCCCTCCGGC    420

GGAAACATCG GCTATGCTCG CCTGGCTGCT TCCGGCTCTG ACCCTGTCGC TGGATCTTCT    480

GCCACTGTTG CTGGCTGGGG CGCTACCTCT GAGGGCGGCA GCTCTACTCC CGTCAACCTT    540

CTGAAGGTTA CTGTCCCTAT CGTCTCTCGT GCTACCTGCC GAGCTCAGTA CGGCACCTCC    600

GCCATCACCA ACCAGATGTT CTGTGCTGGT GTTTCTTCCG GTGGCAAGGA CTCTTGCCAG    660

GGTGACAGCG GCGGCCCCAT CGTCGACAGC TCCAACACTC TTATCGGTGC TGTCTCTTGG    720

GGTAACGGAT GTGCCCGACC CAACTACTCT GGTGTCTATG CCAGCGTTGG TGCTCTCCGC    780

TCTTTCATTG ACACCTATGC TTAAATACCT TGTTGGAAGC GTCGAGATGT TCCTTGAATA    840

TTCTCTAGCT TGAGTCTTGG ATACGAAACC TGTTTGAGAA ATAGGTTTCA ACGAGTTAAG    900

AAGATATGAG TTGATTTCAG TTGGATCTTA GTCCTGGTTG CTCGTAATAG AGCAATCTAG    960

ATAGCCCAAA TTGAATATGA AATTTGATGA AAATATTC                            998
```

(2) INFORMATION FOR SEQ ID NO:4:

(i) SEQUENCE CHARACTERISTICS:
(A) LENGTH: 248 amino acids
(B) TYPE: amino acid
(C) STRANDEDNESS: single
(D) TOPOLOGY: linear (ix) FEATURE:
(A) NAME/KEY: Protein
(B) LOCATION: 1..224

(ix) FEATURE:
(A) NAME/KEY: Peptide
(B) LOCATION: -24..0
(D) OTHER INFORMATION: /product= "OTHER"
/note= "Label=pre-propeptide"

(xi) SEQUENCE DESCRIPTION: SEQ ID NO:4:

```
Met Val Lys Phe Ala Ser Val Val Ala Leu Val Ala Pro Leu Ala Ala
                -20                 -15                 -10

Ala Ala Pro Gln Glu Ile Pro Asn Ile Val Gly Gly Thr Ser Ala Ser
            -5                  1               5

Ala Gly Asp Phe Pro Phe Ile Val Ser Ile Ser Arg Asn Gly Gly Pro
    10                  15                  20

Trp Cys Gly Gly Ser Leu Leu Asn Ala Asn Thr Val Leu Thr Ala Ala
25                  30                  35                  40

His Cys Val Ser Gly Tyr Ala Gln Ser Gly Phe Gln Ile Arg Ala Gly
                45                  50                  55
```

-continued

```
Ser Leu Ser Arg Thr Ser Gly Gly Ile Thr Ser Ser Leu Ser Ser Val
            60                  65                  70

Arg Val His Pro Ser Tyr Ser Gly Asn Asn Asn Asp Leu Ala Ile Leu
        75                  80                  85

Lys Leu Ser Thr Ser Ile Pro Ser Gly Gly Asn Ile Gly Tyr Ala Arg
    90                  95                 100

Leu Ala Ala Ser Gly Ser Asp Pro Val Ala Gly Ser Ser Ala Thr Val
105                 110                 115                 120

Ala Gly Trp Gly Ala Thr Ser Glu Gly Gly Ser Ser Thr Pro Val Asn
                125                 130                 135

Leu Leu Lys Val Thr Val Pro Ile Val Ser Arg Ala Thr Cys Arg Ala
            140                 145                 150

Gln Tyr Gly Thr Ser Ala Ile Thr Asn Gln Met Phe Cys Ala Gly Val
        155                 160                 165

Ser Ser Gly Gly Lys Asp Ser Cys Gln Gly Asp Ser Gly Gly Pro Ile
    170                 175                 180

Val Asp Ser Ser Asn Thr Leu Ile Gly Ala Val Ser Trp Gly Asn Gly
185                 190                 195                 200

Cys Ala Arg Pro Asn Tyr Ser Gly Val Tyr Ala Ser Val Gly Ala Leu
                205                 210                 215

Arg Ser Phe Ile Asp Thr Tyr Ala
            220
```

(2) INFORMATION FOR SEQ ID NO:5:

(i) SEQUENCE CHARACTERISTICS:
(A) LENGTH: 1206 base pairs
(B) TYPE: nucleic acid
(C) STRANDEDNESS: single
(D) TOPOLOGY: linear (xi) SEQUENCE DESCRIPTION: SEQ ID NO:5:

```
GAATTCTTAC AAACCTTCAA CAGTGGAGAC TTCCGACACG ACATATCGAT CCTTTGAAGA     60

TACGGTGAGC GTCAGATCAT GAATTTCATA CATCCTCACG TCCTTCCTCT TTCAAACTAT    120

GCAAAGTCCT TCTAGTACCT CCCAAAACTT GATTTACGCG CTCTCCAATC AAAAGTACCT    180

TCCAAAAGTG ATCTACCTCA GCTCTAGATC AGGGCACCTA TTCGCAAAGA TCTACAAGCT    240

GAACTAGTAA GCATAGCGGG AGAATATCCC ACATCATTCG AGAAGGCCTT CGTATTAGAC    300

CTAGTGGGAT CGACAGAAAA GATAAGACGG AGATAGATGC TATGTTTGGA AGGTAGGGGA    360

TGGAATAGGA TGCAACAGGT ATTGGCATAA GCGATGCAAT AGGTGCATCT AGAAACTAGG    420

TGACAGACTG GCCACAGAGG TGTATCCTAT GCAGGTCGAT GCGTGCGTTA TCGCAGGGCT    480

GCTATTGCGT GGTGGTGGCT ACAAAAGTTC TATGTGGTTT CCAGTTTCAG AATATTGGGC    540

CATTGTGATT GATGGCGCAT GACCGAATTA TAGCAGTGAA CCCCGCCCAG AGTAGTAGTG    600

CAGATGCGCT TTGATGCTTG GCGATTCCTC GGGCTAAATA ACTCCGGTTG GTCTGTAGAA    660

TGCTGACGCG ATGATCCTTC GGCATTAATC GTAGATCTTG GGGGGGGATA AGCCGATCAA    720

AGACACACTG TAGATCAGCT CTTCGATGAC TCTTACCAGC TTTATAATAA CATTCATCTT    780

GAACGTCTTT TTCGTCCAGT GTTTACCTTT CGTCCTATTT ATCCGTCATA TCCACAGTGT    840

TATTGGCGAT AGAGTTATCG ACTTTCCTCA TCGGGATACT GGCCCCTGCT GCCAAGGGCC    900

TTATATGCCG ATCACTTTCA CGGGAGCATG ATAAGGTTAA TGCTTCTTCT GAATGCCGAA    960

CTAGACTACG GAACAACGGA GCTTAGTACC AGAAAGGCAG GTACGCCTAT TCGCAAACTC   1020

CGAAGATACA ACCAAGCAAG CTTATCGCGG GATAGTAACC AGAGAGGCAG GTAAGAAGAC   1080
```

-continued

```
ACAACAACAT CCATAGCTAT GTAGATTCTC GAATATAAAA GGACCAAGAT GGACTATTCG   1140

AAGTAGTCTA TCATCAACCA CTCTTCACTC TTCAACTCTC CTCTCTTGGA TATCTATCTC   1200

TTCACC                                                              1206
```

(2) INFORMATION FOR SEQ ID NO:6:

(i) SEQUENCE CHARACTERISTICS:
(A) LENGTH: 1188 base pairs
(B) TYPE: nucleic acid
(C) STRANDEDNESS: single
(D) TOPOLOGY: linear (xi) SEQUENCE DESCRIPTION: SEQ ID NO:6:

```
TAAATACCTT GTTGGAAGCG TCGAGATGTT CCTTGAATAT TCTCTAGCTT GAGTCTTGGA     60

TACGAAACCT GTTTGAGAAA TAGGTTTCAA CGAGTTAAGA AGATATGAGT TGATTTCAGT    120

TGGATCTTAG TCCTGGTTGC TCGTAATAGA GCAATCTAGA TAGCCCAAAT TGAATATGAA    180

ATTTGATGGA AATATTCATT TCGATAGAAG CAACGTGAAA TGTCTAGCAG GACGAAAAGT    240

AGATCAAGGC TGTTATGTTC CCCGACCAAC CTACCTTGAT GTCAGTCTGC GAGTCGTGTG    300

CAGTGACCCA GAATGATGGA TTGACTTGGA CATTTTCTGT CTATGAAGTA TTATGAACAT    360

GAATATCGTT TCCTCATTAT CTATGTTGGC AGCCTAAAGT TTTACCATAT AGCTAGCAAT    420

CAGTCAAGTA TCTGCGTATG AAGGGTTGTT AAGCCAGGAC GGTATCAGCG TTGAATATTT    480

AAAGAATGAT ATGAGATAAT CAACATTGAC ATGATAAAAG AAAAGGGGAA ACAAATTGTG    540

CATATAGTAA AGACTTCAGG TCGACCCCTC AATAGACATA TGCGAACCGA AAACCAACAG    600

GATACAATTT ATAGATAAGT ATAACTACAG TTATCTGTCT GCCGAACAAA TACTCTTTTG    660

TGAAACAAAT GAAGAGTACA TAAGCTACAG TTCCTCAGTA GGAACATCCT TTACAATAAC    720

TCCCTTGACT TCCTTCAGCT TCTCAATAGC CTCCAAAGTC ATCGGTCTGC CATCAAGGCA    780

CGTCAGCTCT GGTGTAGCAT ACAGCAGTGC CATACTTACG GAGGATAGGA AGTGGGAGGA    840

ATCGTTCGTG TCTGCCTCCA AAAATCGACA CCAGTGTCCT TTTTGACGAT ACTGATATGG    900

TGGTAAGCTT GGGAGTCTAT TGTTGACGTT GCATCACTTA CTTAAGCACG GTTTCATTCC    960

TCTGCTGATA GTCCTCCAAC TTCTCGAAGT CGTAAACGAT GGCCTATAGT ATCTTATTGA   1020

GAAATATGTC TTCTCAGAAA ATTATATCTT GTTTACCTTT CGGTCCGCCA TGGCTGCTAA   1080

AACTGCTGGG AAATTCAAAA GCGCAGCACA AGCAGCAAGA GTGATGGGCA CAACGTGATA   1140

TGTTGATAAA AGCATCAGTA TCGATAAGTT CCACTCAGAA ACCTGCAG                1188
```

(2) INFORMATION FOR SEQ ID NO:7:

(i) SEQUENCE CHARACTERISTICS:
(A) LENGTH: 1060 base pairs
(B) TYPE: nucleic acid
(C) STRANDEDNESS: single
(D) TOPOLOGY: linear (ix) FEATURE:
(A) NAME/KEY: CDS
(B) LOCATION: 10..924

(ix) FEATURE:
(A) NAME/KEY: mat_peptide
(B) LOCATION: 73..924

(ix) FEATURE:
(A) NAME/KEY: sig_peptide
(B) LOCATION: 10..72

-continued (xi) SEQUENCE DESCRIPTION: SEQ ID NO:7:

```
GGATCCAAG ATG CGT TCC TCC CCC CTC CTC CCG TCC GCC GTT GTG GCC          48
          Met Arg Ser Ser Pro Leu Leu Pro Ser Ala Val Val Ala
          -21 -20                 -15                 -10

GCC CTG CCG GTG TTG GCC CTT GCC GCT GAT GGC AGG TCC ACC CGC TAC        96
Ala Leu Pro Val Leu Ala Leu Ala Ala Asp Gly Arg Ser Thr Arg Tyr
             -5                   1               5

TGG GAC TGC TGC AAG CCT TCG TGC GGC TGG GCC AAG AAG GCT CCC GTG       144
Trp Asp Cys Cys Lys Pro Ser Cys Gly Trp Ala Lys Lys Ala Pro Val
     10                  15                  20

AAC CAG CCT GTC TTT TCC TGC AAC GCC AAC TTC CAG CGT ATC ACG GAC       192
Asn Gln Pro Val Phe Ser Cys Asn Ala Asn Phe Gln Arg Ile Thr Asp
 25                  30                  35                  40

TTC GAC GCC AAG TCC GGC TGC GAG CCG GGC GGT GTC GCC TAC TCG TGC       240
Phe Asp Ala Lys Ser Gly Cys Glu Pro Gly Gly Val Ala Tyr Ser Cys
                 45                  50                  55

GCC GAC CAG ACC CCA TGG GCT GTG AAC GAC GAC TTC GCG CTC GGT TTT       288
Ala Asp Gln Thr Pro Trp Ala Val Asn Asp Asp Phe Ala Leu Gly Phe
             60                  65                  70

GCT GCC ACC TCT ATT GCC GGC AGC AAT GAG GCG GGC TGG TGC TGC GCC       336
Ala Ala Thr Ser Ile Ala Gly Ser Asn Glu Ala Gly Trp Cys Cys Ala
         75                  80                  85

TGC TAC GAG CTC ACC TTC ACA TCC GGT CCT GTT GCT GGC AAG AAG ATG       384
Cys Tyr Glu Leu Thr Phe Thr Ser Gly Pro Val Ala Gly Lys Lys Met
     90                  95                 100

GTC GTC CAG TCC ACC AGC ACT GGC GGT GAT CTT GGC AGC AAC CAC TTC       432
Val Val Gln Ser Thr Ser Thr Gly Gly Asp Leu Gly Ser Asn His Phe
105                 110                 115                 120

GAT CTC AAC ATC CCC GGC GGC GGC GTC GGC ATC TTC GAC GGA TGC ACT       480
Asp Leu Asn Ile Pro Gly Gly Gly Val Gly Ile Phe Asp Gly Cys Thr
                125                 130                 135

CCC CAG TTC GGC GGT CTG CCC GGC CAG CGC TAC GGC GGC ATC TCG TCC       528
Pro Gln Phe Gly Gly Leu Pro Gly Gln Arg Tyr Gly Gly Ile Ser Ser
            140                 145                 150

CGC AAC GAG TGC GAT CGG TTC CCC GAC GCC CTC AAG CCC GGC TGC TAC       576
Arg Asn Glu Cys Asp Arg Phe Pro Asp Ala Leu Lys Pro Gly Cys Tyr
        155                 160                 165

TGG CGC TTC GAC TGG TTC AAG AAC GCC GAC AAT CCG AGC TTC AGC TTC       624
Trp Arg Phe Asp Trp Phe Lys Asn Ala Asp Asn Pro Ser Phe Ser Phe
    170                 175                 180

CGT CAG GTC CAG TGC CCA GCC GAG CTC GTC GCT CGC ACC GGA TGC CGC       672
Arg Gln Val Gln Cys Pro Ala Glu Leu Val Ala Arg Thr Gly Cys Arg
185                 190                 195                 200

CGC AAC GAC GAC GGC AAC TTC CCT GCC GTC CAG ATC CCC TCC AGC AGC       720
Arg Asn Asp Asp Gly Asn Phe Pro Ala Val Gln Ile Pro Ser Ser Ser
                205                 210                 215

ACC AGC TCT CCG GTC AAC CAG CCT ACC AGC ACC AGC ACC ACG TCC ACC       768
Thr Ser Ser Pro Val Asn Gln Pro Thr Ser Thr Ser Thr Thr Ser Thr
            220                 225                 230

TCC ACC ACC TCG AGC CCG CCA GTC CAG CCT ACG ACT CCC AGC GGC TGC       816
Ser Thr Thr Ser Ser Pro Pro Val Gln Pro Thr Thr Pro Ser Gly Cys
        235                 240                 245

ACT GCT GAG AGG TGG GCT CAG TGC GGC GGC AAT GGC TGG AGC GGC TGC       864
Thr Ala Glu Arg Trp Ala Gln Cys Gly Gly Asn Gly Trp Ser Gly Cys
    250                 255                 260

ACC ACC TGC GTC GCT GGC AGC ACT TGC ACG AAG ATT AAT GAC TGG TAC       912
Thr Thr Cys Val Ala Gly Ser Thr Cys Thr Lys Ile Asn Asp Trp Tyr
265                 270                 275                 280

CAT CAG TGC CTG TAGACGCAGG GCAGCTTGAG GGCCTTACTG GTGGCCGCAA           964
```

-continued

```
His Gln Cys Leu

CGAAATGACA CTCCCAATCA CTGTATTAGT TCTTGTACAT AATTTCGTCA TCCCTCCAGG   1024

GATTGTCACA TAAATGCAAT GAGGAACAAT GAGTAC                             1060


(2) INFORMATION FOR SEQ ID NO:8:

     (i) SEQUENCE CHARACTERISTICS:
          (A) LENGTH: 305 amino acids
          (B) TYPE: amino acid
          (D) TOPOLOGY: linear

    (ii) MOLECULE TYPE: protein

    (xi) SEQUENCE DESCRIPTION: SEQ ID NO:8:

Met Arg Ser Ser Pro Leu Leu Pro Ser Ala Val Val Ala Ala Leu Pro
-21 -20                 -15                 -10

Val Leu Ala Leu Ala Ala Asp Gly Arg Ser Thr Arg Tyr Trp Asp Cys
 -5                   1               5                  10

Cys Lys Pro Ser Cys Gly Trp Ala Lys Lys Ala Pro Val Asn Gln Pro
             15                  20                  25

Val Phe Ser Cys Asn Ala Asn Phe Gln Arg Ile Thr Asp Phe Asp Ala
         30                  35                  40

Lys Ser Gly Cys Glu Pro Gly Gly Val Ala Tyr Ser Cys Ala Asp Gln
     45                  50                  55

Thr Pro Trp Ala Val Asn Asp Asp Phe Ala Leu Gly Phe Ala Ala Thr
 60                  65                  70                  75

Ser Ile Ala Gly Ser Asn Glu Ala Gly Trp Cys Cys Ala Cys Tyr Glu
                 80                  85                  90

Leu Thr Phe Thr Ser Gly Pro Val Ala Gly Lys Lys Met Val Val Gln
             95                 100                 105

Ser Thr Ser Thr Gly Gly Asp Leu Gly Ser Asn His Phe Asp Leu Asn
        110                 115                 120

Ile Pro Gly Gly Gly Val Gly Ile Phe Asp Gly Cys Thr Pro Gln Phe
    125                 130                 135

Gly Gly Leu Pro Gly Gln Arg Tyr Gly Gly Ile Ser Ser Arg Asn Glu
140                 145                 150                 155

Cys Asp Arg Phe Pro Asp Ala Leu Lys Pro Gly Cys Tyr Trp Arg Phe
                160                 165                 170

Asp Trp Phe Lys Asn Ala Asp Asn Pro Ser Phe Ser Phe Arg Gln Val
            175                 180                 185

Gln Cys Pro Ala Glu Leu Val Ala Arg Thr Gly Cys Arg Arg Asn Asp
        190                 195                 200

Asp Gly Asn Phe Pro Ala Val Gln Ile Pro Ser Ser Ser Thr Ser Ser
    205                 210                 215

Pro Val Asn Gln Pro Thr Ser Thr Ser Thr Thr Ser Thr Ser Thr Thr
220                 225                 230                 235

Ser Ser Pro Pro Val Gln Pro Thr Thr Pro Ser Gly Cys Thr Ala Glu
                240                 245                 250

Arg Trp Ala Gln Cys Gly Gly Asn Gly Trp Ser Gly Cys Thr Thr Cys
            255                 260                 265

Val Ala Gly Ser Thr Cys Thr Lys Ile Asn Asp Trp Tyr His Gln Cys
        270                 275                 280

Leu


(2) INFORMATION FOR SEQ ID NO:9:
```

-continued (i) SEQUENCE CHARACTERISTICS:
(A) LENGTH: 876 base pairs
(B) TYPE: nucleic acid
(C) STRANDEDNESS: single
(D) TOPOLOGY: linear (xi) SEQUENCE DESCRIPTION: SEQ ID NO:9:

```
ATGAGGAGCT CCCTTGTGCT GTTCTTTGTC TCTGCGTGGA CGGCCTTGGC CAGTCCTATT     60

CGTCGAGAGG TCTCGCAGGA TCTGTTTAAC CAGTTCAATC TCTTTGCACA GTATTCTGCA    120

GCCGCATACT GCGGAAAAAA CAATGATGCC CCAGCTGGTA CAAACATTAC GTGCACGGGA    180

AATGCCTGCC CCGAGGTAGA GAAGGCGGAT GCAACGTTTC TCTACTCGTT TGAAGACTCT    240

GGAGTGGGCG ATGTCACCGG CTTCCTTGCT CTCGACAACA CGAACAAATT GATCGTCCTC    300

TCTTTCCGTG GCTCTCGTTC CATAGAGAAC TGGATCGGGA ATCTTAACTT CGACTTGAAA    360

GAAATAAATG ACATTTGCTC CGGCTGCAGG GGACATGACG GCTTCACTTC GTCCTGGAGG    420

TCTGTAGCCG ATACGTTAAG GCAGAAGGTG GAGGATGCTG TGAGGGAGCA TCCCGACTAT    480

CGCGTGGTGT TTACCGGACA TAGCTTGGGT GGTGCATTGG CAACTGTTGC CGGAGCAGAC    540

CTGCGTGGAA ATGGGTATGA TATCGACGTG TTTTCATATG GCGCCCCCCG AGTCGGAAAC    600

AGGGCTTTTG CAGAATTCCT GACCGTACAG ACCGGCGGAA CACTCTACCG CATTACCCAC    660

ACCAATGATA TTGTCCCTAG ACTCCCGCCG CGCGAATTCG GTTACAGCCA TTCTAGCCCA    720

GAGTACTGGA TCAAATCTGG AACCCTTGTC CCCGTCACCC GAAACGATAT CGTGAAGATA    780

GAAGGCATCG ATGCCACCGG CGGCAATAAC CAGCCTAACA TTCCGGATAT CCCTGCGCAC    840

CTATGGTACT TCGGGTTAAT TGGGACATGT CTTTAG                              876
```

(2) INFORMATION FOR SEQ ID NO:10:

(i) SEQUENCE CHARACTERISTICS:
(A) LENGTH: 291 amino acids
(B) TYPE: amino acid
(C) STRANDEDNESS: single
(D) TOPOLOGY: linear (xi) SEQUENCE DESCRIPTION: SEQ ID NO:10:

```
Met Arg Ser Ser Leu Val Leu Phe Phe Val Ser Ala Trp Thr Ala Leu
1               5                   10                  15

Ala Ser Pro Ile Arg Arg Glu Val Ser Gln Asp Leu Phe Asn Gln Phe
            20                  25                  30

Asn Leu Phe Ala Gln Tyr Ser Ala Ala Ala Tyr Cys Gly Lys Asn Asn
        35                  40                  45

Asp Ala Pro Ala Gly Thr Asn Ile Thr Cys Thr Gly Asn Ala Cys Pro
    50                  55                  60

Glu Val Glu Lys Ala Asp Ala Thr Phe Leu Tyr Ser Phe Glu Asp Ser
65                  70                  75                  80

Gly Val Gly Asp Val Thr Gly Phe Leu Ala Leu Asp Asn Thr Asn Lys
                85                  90                  95

Leu Ile Val Leu Ser Phe Arg Gly Ser Arg Ser Ile Glu Asn Trp Ile
            100                 105                 110

Gly Asn Leu Asn Phe Asp Leu Lys Glu Ile Asn Asp Ile Cys Ser Gly
        115                 120                 125

Cys Arg Gly His Asp Gly Phe Thr Ser Ser Trp Arg Ser Val Ala Asp
    130                 135                 140

Thr Leu Arg Gln Lys Val Glu Asp Ala Val Arg Glu His Pro Asp Tyr
145                 150                 155                 160
```

-continued

```
Arg Val Val Phe Thr Gly His Ser Leu Gly Gly Ala Leu Ala Thr Val
                165                 170                 175

Ala Gly Ala Asp Leu Arg Gly Asn Gly Tyr Asp Ile Asp Val Phe Ser
            180                 185                 190

Tyr Gly Ala Pro Arg Val Gly Asn Arg Ala Phe Ala Glu Phe Leu Thr
        195                 200                 205

Val Gln Thr Gly Gly Thr Leu Tyr Arg Ile Thr His Thr Asn Asp Ile
    210                 215                 220

Val Pro Arg Leu Pro Pro Arg Glu Phe Gly Tyr Ser His Ser Ser Pro
225                 230                 235                 240

Glu Tyr Trp Ile Lys Ser Gly Thr Leu Val Pro Val Thr Arg Asn Asp
                245                 250                 255

Ile Val Lys Ile Glu Gly Ile Asp Ala Thr Gly Gly Asn Asn Gln Pro
            260                 265                 270

Asn Ile Pro Asp Ile Pro Ala His Leu Trp Tyr Phe Gly Leu Ile Gly
        275                 280                 285

Thr Cys Leu
    290
```

(2) INFORMATION FOR SEQ ID NO:11:

(i) SEQUENCE CHARACTERISTICS:
(A) LENGTH: 42 base pairs
(B) TYPE: nucleic acid
(C) STRANDEDNESS: single
(D) TOPOLOGY: linear (xi) SEQUENCE DESCRIPTION: SEQ ID NO:11:

GCACACCATG GTCGCTGGAT CCATACCTTG TTGGAAGCGT CG 42

(2) INFORMATION FOR SEQ ID NO:12:

(i) SEQUENCE CHARACTERISTICS:
(A) LENGTH: 56 base pairs
(B) TYPE: nucleic acid
(C) STRANDEDNESS: single
(D) TOPOLOGY: linear (xi) SEQUENCE DESCRIPTION: SEQ ID NO:12:

ATCGGAGCAT GCGGTACCGT TTAAACGAAT TCAGGTAAAC AAGATATAAT TTTCTG 56

(2) INFORMATION FOR SEQ ID NO:13:

(i) SEQUENCE CHARACTERISTICS:
(A) LENGTH: 44 base pairs
(B) TYPE: nucleic acid
(C) STRANDEDNESS: single
(D) TOPOLOGY: linear (xi) SEQUENCE DESCRIPTION: SEQ ID NO:13:

CTCTTGGATA TCTATCTCTT CACCATGCGT TCCTCCCCCC TCCT 44

(2) INFORMATION FOR SEQ ID NO:14:

(i) SEQUENCE CHARACTERISTICS:
(A) LENGTH: 20 base pairs
(B) TYPE: nucleic acid
(C) STRANDEDNESS: single
(D) TOPOLOGY: linear -continued

```
    (xi) SEQUENCE DESCRIPTION: SEQ ID NO:14:

CAATAGAGGT GGCAGCAAAA                                                    20

(2) INFORMATION FOR SEQ ID NO:15:

     (i) SEQUENCE CHARACTERISTICS:
          (A) LENGTH: 25 base pairs
          (B) TYPE: nucleic acid
          (C) STRANDEDNESS: single
          (D) TOPOLOGY: linear

    (xi) SEQUENCE DESCRIPTION: SEQ ID NO:15:

ATCTATCTCT TCACCATGAG GAGCT                                              25

(2) INFORMATION FOR SEQ ID NO:16:

     (i) SEQUENCE CHARACTERISTICS:
          (A) LENGTH: 21 base pairs
          (B) TYPE: nucleic acid
          (C) STRANDEDNESS: single
          (D) TOPOLOGY: linear

    (xi) SEQUENCE DESCRIPTION: SEQ ID NO:16:

TAGATAGAGA AGTGGTACTC C                                                  21
```